United States Patent
Nikolis et al.

(10) Patent No.: US 10,207,029 B2
(45) Date of Patent: Feb. 19, 2019

(54) TISSUE FILLER COMPOSITIONS AND METHODS OF USE

(71) Applicant: KLOX Technologies Inc., Laval (CA)

(72) Inventors: Andreas Nikolis, Westmount (CA); Lise Hébert, Montréal (CA)

(73) Assignee: KLOX TECHNOLOGIES INC., Laval, Quebec (CA)

( * ) Notice: Subject to any disclaimer, the term of this patent is extended or adjusted under 35 U.S.C. 154(b) by 0 days.

(21) Appl. No.: 15/301,189

(22) PCT Filed: Apr. 1, 2015

(86) PCT No.: PCT/CA2015/050261
§ 371 (c)(1),
(2) Date: Sep. 30, 2016

(87) PCT Pub. No.: WO2015/149177
PCT Pub. Date: Oct. 8, 2015

(65) Prior Publication Data
US 2017/0014549 A1    Jan. 19, 2017

Related U.S. Application Data

(60) Provisional application No. 61/973,659, filed on Apr. 1, 2014.

(51) Int. Cl.
*A61L 27/50* (2006.01)
*A61K 41/00* (2006.01)
(Continued)

(52) U.S. Cl.
CPC .............. *A61L 27/50* (2013.01); *A61K 8/498* (2013.01); *A61K 8/735* (2013.01); *A61K 41/00* (2013.01);
(Continued)

(58) Field of Classification Search
CPC ....................................................... A61K 5/40
See application file for complete search history.

(56) References Cited

U.S. PATENT DOCUMENTS 2,877,221 A    3/1959    Lanbach
3,293,127 A    12/1966    Beck
(Continued)

FOREIGN PATENT DOCUMENTS

CA    2166527 A1    7/1996
CA    2222027 A1    6/1998
(Continued)

OTHER PUBLICATIONS

Alster, et al., "Photodynamic therapy: practical cosmetic applications," Journal of Drugs in Dermatology, 5(8):764-768 (2006).
(Continued)

*Primary Examiner* — Benjamin J Packard
(74) *Attorney, Agent, or Firm* — BCF LLP

(57) ABSTRACT

The present disclosure relates to methods for stimulating collagen synthesis, cosmetic enhancement of soft tissue and/or inhibiting or treating scarring comprising administering a composition to an area to be treated within a soft tissue, wherein the composition comprises a tissue filler medium and a fluorophore; and illuminating the area with light having a wavelength which can be absorbed by the fluorophore.

26 Claims, 4 Drawing Sheets

(51) Int. Cl.
- *A61K 8/49* (2006.01)
- *A61K 8/73* (2006.01)
- *A61Q 19/08* (2006.01)
- *A61L 27/52* (2006.01)
- *A61L 27/54* (2006.01)
- *A61N 5/06* (2006.01)
- *A61L 27/20* (2006.01)
- *A61L 27/58* (2006.01)
- *A61B 18/00* (2006.01)

(52) U.S. Cl.
CPC ............. *A61L 27/20* (2013.01); *A61L 27/52* (2013.01); *A61L 27/54* (2013.01); *A61L 27/58* (2013.01); *A61N 5/062* (2013.01); *A61N 5/0616* (2013.01); *A61Q 19/08* (2013.01); *A61B 2018/0047* (2013.01); *A61K 2800/81* (2013.01); *A61K 2800/884* (2013.01); *A61K 2800/91* (2013.01); *A61L 2300/442* (2013.01); *A61L 2400/06* (2013.01); *A61L 2430/34* (2013.01)

(56) References Cited

U.S. PATENT DOCUMENTS

| | | |
|---|---|---|
| 3,309,274 A | 3/1967 | Brilliant |
| 3,372,125 A | 3/1968 | Hill |
| 3,595,798 A | 7/1971 | Smith et al. |
| 3,597,362 A | 8/1971 | Rauhut et al. |
| 3,652,420 A | 3/1972 | Hill |
| 3,671,450 A | 6/1972 | Rauhut et al. |
| 3,728,446 A | 4/1973 | Roberts et al. |
| 4,320,140 A | 3/1982 | Crounse et al. |
| 4,574,097 A | 3/1986 | Honeycutt |
| 4,647,578 A | 3/1987 | Crounse et al. |
| 4,891,211 A | 1/1990 | Winston |
| 4,923,726 A | 5/1990 | Maruyama et al. |
| 4,992,256 A | 2/1991 | Skaggs et al. |
| 5,292,362 A | 3/1994 | Bass et al. |
| 5,516,227 A | 5/1996 | Kozak et al. |
| 5,611,793 A | 3/1997 | Wilson et al. |
| 5,658,148 A | 8/1997 | Neuberger et al. |
| 5,723,148 A | 3/1998 | Love |
| 5,749,968 A | 5/1998 | Melanson et al. |
| 5,785,527 A | 7/1998 | Jensen et al. |
| 5,844,016 A | 12/1998 | Sawhney et al. |
| 5,858,332 A | 1/1999 | Jensen et al. |
| 5,885,557 A | 3/1999 | Lentini |
| 5,922,331 A | 7/1999 | Mausner |
| 6,030,222 A | 2/2000 | Tarver |
| 6,036,493 A | 3/2000 | Sharma |
| 6,107,466 A | 8/2000 | Hasan et al. |
| 6,121,341 A | 9/2000 | Sawhney et al. |
| 6,149,895 A | 11/2000 | Kutsch |
| 6,162,055 A | 12/2000 | Montgomery et al. |
| 6,254,388 B1 | 7/2001 | Yarborough |
| 6,267,976 B1 | 7/2001 | Barnhart et al. |
| 6,343,933 B1 | 2/2002 | Montgomery et al. |
| 6,361,329 B1 | 3/2002 | Dekker et al. |
| 6,365,134 B1 | 4/2002 | Orlowski et al. |
| 6,387,353 B1 | 5/2002 | Jensen et al. |
| 6,391,283 B1 | 5/2002 | Jensen et al. |
| 6,420,455 B1 | 7/2002 | Landgrebe et al. |
| 6,440,396 B1 | 8/2002 | McLaughlin |
| 6,485,709 B2 | 11/2002 | Banerjee et al. |
| 6,541,460 B2 | 4/2003 | Petito |
| 6,558,653 B2 | 5/2003 | Andersen et al. |
| 6,905,672 B2 | 6/2005 | Rajaiah et al. |
| 7,066,941 B2 | 6/2006 | Perricone |
| 7,081,128 B2 | 7/2006 | Hart et al. |
| 7,255,691 B2 | 8/2007 | Tolkoff et al. |
| 7,314,470 B2 | 1/2008 | Malodobry |
| 7,354,448 B2 | 4/2008 | Altshuler et al. |
| 8,075,875 B2 | 12/2011 | Piergallini et al. |
| 8,124,120 B2 | 2/2012 | Sadozai et al. |
| 8,182,473 B2 | 5/2012 | Altshuler et al. |
| 8,632,822 B2 | 1/2014 | Piergallini et al. |
| 8,637,086 B2 | 1/2014 | Piergallini et al. |
| 8,658,219 B2 | 2/2014 | Piergallini et al. |
| 8,685,466 B2 | 4/2014 | Piergallini et al. |
| 8,911,791 B2 | 12/2014 | Piergallini et al. |
| 8,974,833 B2 | 3/2015 | Piergallini et al. |
| 8,986,719 B2 | 3/2015 | Piergallini et al. |
| 8,986,745 B2 | 3/2015 | Piergallini et al. |
| 8,986,746 B2 | 3/2015 | Piergallini et al. |
| 9,345,648 B2 | 5/2016 | Piergallini et al. |
| 9,375,446 B2 | 6/2016 | Piergallini et al. |
| 2001/0022970 A1 | 9/2001 | Dees et al. |
| 2002/0029071 A1 | 3/2002 | Whitehurst |
| 2003/0004499 A1 | 1/2003 | McDaniel |
| 2003/0148995 A1 | 8/2003 | Piron et al. |
| 2003/0198605 A1 | 10/2003 | Montgomery |
| 2004/0010299 A1 | 1/2004 | Tolkoff et al. |
| 2004/0136971 A1 | 7/2004 | Scharp et al. |
| 2004/0147984 A1 | 7/2004 | Altshuler et al. |
| 2004/0191330 A1 | 9/2004 | Keefe et al. |
| 2004/0193234 A1 | 9/2004 | Butler |
| 2004/0262569 A1 | 12/2004 | Cho et al. |
| 2005/0020696 A1 | 1/2005 | Montgomery et al. |
| 2005/0026298 A1 | 2/2005 | Bickett et al. |
| 2005/0042712 A1 | 2/2005 | Huth et al. |
| 2005/0049228 A1 | 3/2005 | Albrecht et al. |
| 2005/0059731 A1 | 3/2005 | Albrecht et al. |
| 2005/0098766 A1 | 5/2005 | Watson et al. |
| 2005/0100514 A1 | 5/2005 | Sakaguchi et al. |
| 2005/0123588 A1 | 6/2005 | Zhu et al. |
| 2005/0124721 A1 | 6/2005 | Arthur et al. |
| 2005/0124722 A1 | 6/2005 | Arthur et al. |
| 2005/0249677 A1 | 11/2005 | Malcmacher et al. |
| 2005/0261750 A1 | 11/2005 | McDaniel |
| 2006/0099155 A1 | 5/2006 | MacDonald et al. |
| 2006/0194758 A1 | 8/2006 | Lebreton |
| 2006/0198796 A1 | 9/2006 | Giniger et al. |
| 2006/0199242 A1 | 9/2006 | Cheung et al. |
| 2006/0217690 A1 | 9/2006 | Bastin |
| 2006/0228320 A1 | 10/2006 | Minami |
| 2006/0251687 A1 | 11/2006 | Lapidot et al. |
| 2006/0287211 A1 | 12/2006 | Barbizan et al. |
| 2007/0021807 A1 | 1/2007 | Kurtz |
| 2007/0092469 A1 | 4/2007 | Jacobs |
| 2007/0128132 A1 | 6/2007 | Piergallini et al. |
| 2007/0148623 A1 | 6/2007 | Dias et al. |
| 2007/0166369 A1 | 7/2007 | Neuberger et al. |
| 2007/0191249 A1 | 8/2007 | Lant |
| 2007/0244195 A1 | 10/2007 | Burkhart et al. |
| 2007/0286824 A1 | 12/2007 | Rabe et al. |
| 2008/0058689 A1 | 3/2008 | Holloway et al. |
| 2008/0089918 A1 | 4/2008 | Lebreton |
| 2008/0091250 A1 | 4/2008 | Powell |
| 2008/0096857 A1 | 4/2008 | Curaudeau et al. |
| 2008/0108681 A1 | 5/2008 | Scimeca et al. |
| 2008/0113037 A1 | 5/2008 | Green et al. |
| 2008/0118578 A1 | 5/2008 | Dees et al. |
| 2008/0206159 A1 | 8/2008 | Tamarkin et al. |
| 2008/0255498 A1 | 10/2008 | Houle |
| 2008/0305101 A1 | 12/2008 | Ruoslahti et al. |
| 2009/0074868 A1* | 3/2009 | Elisseeff ............ A61K 8/02 424/486 |
| 2009/0088824 A1 | 4/2009 | Baird et al. |
| 2009/0130030 A1 | 5/2009 | Ribi |
| 2009/0162423 A1 | 6/2009 | Neuberger et al. |
| 2009/0220450 A1 | 9/2009 | Green et al. |
| 2009/0238778 A1 | 9/2009 | Mordas et al. |
| 2009/0269121 A1 | 10/2009 | Snedden et al. |
| 2009/0286886 A1 | 11/2009 | Fisher et al. |
| 2010/0028438 A1 | 2/2010 | Lebreton |
| 2010/0152296 A1 | 6/2010 | Marmarinos et al. |
| 2010/0227799 A1 | 9/2010 | Trudel |
| 2010/0255045 A1 | 10/2010 | Eymard Du Vernet |
| 2010/0266989 A1 | 10/2010 | Piergallini et al. |
| 2010/0277105 A1 | 11/2010 | Oyama |
| 2011/0027753 A1 | 2/2011 | Maurat et al. |
| 2011/0171310 A1 | 7/2011 | Gousse et al. |

(56) References Cited

U.S. PATENT DOCUMENTS

| | | | |
|---|---|---|---|
| 2011/0245748 A1 | 10/2011 | Rinke | |
| 2011/0319808 A1 | 12/2011 | Bowler et al. | |
| 2012/0045516 A1 | 2/2012 | Kim et al. | |
| 2012/0095455 A1 | 4/2012 | Rodmond et al. | |
| 2012/0171641 A1 | 7/2012 | Piergallini et al. | |
| 2013/0122467 A1 | 5/2013 | Piergallini et al. | |
| 2013/0281913 A1 | 10/2013 | Piergallini et al. | |
| 2014/0039062 A1 | 2/2014 | Stroumpoulis et al. | |
| 2014/0276354 A1 | 9/2014 | Piergallini et al. | |
| 2014/0303547 A1 | 10/2014 | Loupis et al. | |
| 2015/0065453 A1 | 3/2015 | Piergallini et al. | |
| 2015/0119788 A1 | 4/2015 | Loupis et al. | |
| 2015/0246127 A1 | 9/2015 | Loupis et al. | |
| 2015/0290103 A1 | 10/2015 | Piergallini et al. | |
| 2015/0290320 A1 | 10/2015 | Piergallini et al. | |
| 2015/0306131 A1 | 10/2015 | Piergallini et al. | |
| 2015/0360047 A1 | 12/2015 | Loupis et al. | |
| 2016/0030564 A1 | 2/2016 | Loupis et al. | |
| 2016/0136075 A1 | 5/2016 | Loupis et al. | |
| 2017/0027833 A1 | 2/2017 | Piergallini et al. | |
| 2017/0112755 A1 | 4/2017 | Piergallini et al. | |

FOREIGN PATENT DOCUMENTS

| | | |
|---|---|---|
| CA | 2360202 A1 | 7/2000 |
| CA | 2457590 A1 | 3/2003 |
| CA | 2551613 A1 | 12/2005 |
| CA | 2580381 A1 | 1/2006 |
| CA | 2677468 A1 | 8/2008 |
| CA | 2695386 A1 | 2/2009 |
| CA | 2706808 A1 | 8/2009 |
| CA | 2742942 A1 | 5/2010 |
| CA | 2742943 A1 | 5/2010 |
| CA | 2745059 A1 | 6/2010 |
| CA | 2809405 A1 | 1/2012 |
| CA | 2868893 A1 | 10/2013 |
| CA | 2873068 A1 | 12/2013 |
| CA | 2883717 A1 | 3/2014 |
| CN | 102133208 A | 7/2011 |
| DE | 2935450 A1 | 3/1981 |
| EP | 0356868 A2 | 3/1990 |
| EP | 0380157 A1 | 8/1990 |
| EP | 0704539 A2 | 4/1996 |
| EP | 1235543 A1 | 9/2002 |
| EP | 1235544 A1 | 9/2002 |
| EP | 1749532 A1 | 2/2007 |
| EP | 1779891 A1 | 5/2007 |
| EP | 1951184 A2 | 8/2008 |
| EP | 2338465 A1 | 6/2011 |
| JP | 04-219756 | 8/1922 |
| JP | 01-279838 | 11/1989 |
| JP | H03169805 | 7/1991 |
| JP | H092925 A | 1/1997 |
| JP | H10-182390 A | 7/1998 |
| JP | H10330235 A | 12/1998 |
| JP | 2000053550 A | 2/2000 |
| JP | 2001511137 A | 8/2001 |
| JP | 2002502864 A | 1/2002 |
| JP | 2002226349 A | 8/2002 |
| JP | 2002233612 A | 8/2002 |
| JP | 2002293747 A | 10/2002 |
| JP | 2003339875 A | 12/2003 |
| KR | 10-20070017292 | 2/2007 |
| WO | WO-1981000513 A1 | 3/1981 |
| WO | WO-1990000779 A1 | 9/1990 |
| WO | WO-1991002530 A1 | 3/1991 |
| WO | WO-1993021992 A1 | 11/1993 |
| WO | WO-1997021420 A1 | 6/1997 |
| WO | WO-1998010738 A1 | 3/1998 |
| WO | WO-1998011827 A1 | 3/1998 |
| WO | WO-1998023219 A1 | 6/1998 |
| WO | WO-1998030169 A1 | 7/1998 |
| WO | WO-1998033761 A1 | 8/1998 |
| WO | WO-1998036700 A1 | 8/1998 |
| WO | WO-1999039238 A1 | 8/1999 |
| WO | WO-1999040870 A1 | 8/1999 |
| WO | WO-1999049823 A1 | 10/1999 |
| WO | WO-1999063900 A1 | 12/1999 |
| WO | WO-2000040266 | 7/2000 |
| WO | WO-2001000190 A2 | 1/2001 |
| WO | WO-2001012181 A1 | 2/2001 |
| WO | WO-2002011539 A1 | 2/2002 |
| WO | WO-2002022097 A1 | 3/2002 |
| WO | WO-2002087642 A2 | 11/2002 |
| WO | WO-2003000215 A1 | 1/2003 |
| WO | WO-2003017824 A2 | 3/2003 |
| WO | WO-2003061696 A2 | 7/2003 |
| WO | WO-2003086215 A1 | 10/2003 |
| WO | WO-2003099247 A1 | 12/2003 |
| WO | WO-2004028498 A1 | 4/2004 |
| WO | 2004073759 A1 | 9/2004 |
| WO | WO-2004073540 A2 | 9/2004 |
| WO | WO-2004081222 A2 | 9/2004 |
| WO | WO-2005009604 A1 | 2/2005 |
| WO | WO-2005051305 A2 | 6/2005 |
| WO | WO-2006014597 A1 | 2/2006 |
| WO | WO-2006032847 A1 | 3/2006 |
| WO | WO-2006047868 A1 | 5/2006 |
| WO | WO-2006072243 A1 | 7/2006 |
| WO | WO-2006118835 A2 | 11/2006 |
| WO | WO-2006125650 A1 | 11/2006 |
| WO | WO-2006135344 A1 | 12/2006 |
| WO | WO-2007087259 | 2/2007 |
| WO | WO-2007080453 A2 | 7/2007 |
| WO | WO-2007084468 A2 | 7/2007 |
| WO | WO-2007127172 A2 | 11/2007 |
| WO | WO-2008011707 A1 | 1/2008 |
| WO | WO-2008013962 A2 | 1/2008 |
| WO | WO-2008052081 A2 | 5/2008 |
| WO | WO-2008096182 A1 | 8/2008 |
| WO | WO-2009089345 A2 | 7/2009 |
| WO | WO-2009089346 A2 | 7/2009 |
| WO | WO-2010051636 A1 | 5/2010 |
| WO | WO-2010051641 A1 | 5/2010 |
| WO | WO-2010070292 A1 | 6/2010 |
| WO | WO-2010145696 A1 | 12/2010 |
| WO | WO-2011006263 A1 | 1/2011 |
| WO | WO-2011058448 A2 | 5/2011 |
| WO | WO-2011134087 A1 | 11/2011 |
| WO | WO-2012072980 A1 | 6/2012 |
| WO | WO-2012110178 | 8/2012 |
| WO | WO-2012119131 | 9/2012 |
| WO | WO-2012126120 A1 | 9/2012 |
| WO | WO-2013155620 A1 | 10/2013 |
| WO | WO-2014040176 A1 | 3/2014 |
| WO | WO-2014040177 A1 | 3/2014 |
| WO | WO-2014042936 A2 | 3/2014 |
| WO | WO-2014138930 A1 | 9/2014 |
| WO | WO-2015000058 A1 | 1/2015 |
| WO | WO-2016065488 | 5/2016 |
| WO | WO-2017201615 | 11/2017 |

OTHER PUBLICATIONS

Antunes, et al., "Evaluation of the clastogenicity and anticlastongenicity of the carotenoid bixin in human lymphocyte cultures," Mutation Research, 585(1-2):113-9 (2005).

Ariizumi et al., "Clinical evaluation of a topical applicant TSG-88 for periodontal disease," Dental Drug Therapy, 10(2):157-168 (1991) (English Abstract included).

Berneburg, et al., "Phototherapy with narrowband UVB," Acta Dermato-Venereologica, 85:1-11 (2005).

Chen et al., "Study of the chemiluminescent characteristics of some xanthone dyes," Analytica Chimica Acta, 292(1-2):159-167 (1994).

Clark, et al, "Eosin-Phloxine alcoholic solution," Mitt. Zool. Stat. Neapel, Jan. 1, 1981 (Jan. 1, 1981), pp. 170-186, XP055224968, Retrieved from the Internet: URL:http://tunic.ro/fise/tehnice/05-10020L.pdf * abstract * (1 page).

Colman, et al., "The healing of wounds in the skin of piglets treated with benzoyl peroxide," The Journal of Dermatologic Surgery and Oncology, 4(9):705-707 (1978).

(56) References Cited

OTHER PUBLICATIONS

Darzynkiewicz, et al., "Photosensitizing effects of the tricyclic heteroaromatic cationic dyes Pyronin Y and Toluidine Blue O (tolonium chloride)," Cancer Research, 48(5):1295-1299 (1988).
De, et al., "Environmental effects on the aggregation of some xanthene dyes used in lasers," Spectrochimica Acta Part A: Molecular and Biomolecular Spectroscopy, 61(8):1821-1833 (2005).
Decraene et al., "Cellulose acetate containing Toluidine Blue and Rose Bengal is an effective antimicrobial coating when exposed to white light," Applied and Env. Microbiology, 72:6(4436-4439) (Jun. 2006).
Escobar-Chavez et al., "Applications of thermoreversible pluronic F-127 gels in pharmaceutical formulations", J. Pharm. Pharmaceut. Sci., 2006, 9(3), 339-358.
Eurasian Search Report, Serial No. 201291068, dated May 29, 2013 with English translation (3 pages).
European Search Report and Written Opinion, Application No. EP11161795, dated May 23, 2011 (6 pages).
European Supplementary Search Report, Application No. EP09824320, dated Mar. 28, 2012 (12 pages).
FDA, Color Additive Status List, http://www.cfsanJda.gov/-dms/opa-appc.html, downloaded Jun. 18, 2008 (13 pages).
FDA, Product Classification Database Search, http://www.accessdata.fda.gov/scripts/cdrh/cfdocs/cfpcd/classificiation/c.f?ID-3964, Device: Eosiny: database, downloaded Jun. 18, 2008 (2 pages).
Fisher Scientific, "Material Safety Data Sheet: Sodium acetate buffer," https://fscimagef.fishersci.com/msds/91502.htm (ACC #91502) (Apr. 13, 2000) (5 pages).
Goldberg, "Photodynamic therapy in skin rejuvenation," Clinics in Dermatology, 26(6):608-613 (2008).
Gonzales et al., "Photodynamic inactivation of microorganisms as an innovative approach to kill mucocutaneous and skin microorganisms," Giornale Italiano Di Dermatologia e Venereologia, 145, pp. 477-489 (2010).
Jankowski, et al., "The action of photosensitizers and serum in a bactericidal process. II. The effects of dyes: Hypericin, Eosin Y and Saphranine O," Polish Journal of Microbiology, 54(4):323-330 (2005).
Kelly, et al., "Combined photodynamic and photothermal induced injury enhances damage to in vivo model blood vessels," Lasers in Surgery and Medicine, 34(5):407-413 (2004).
Korb, et al, "An evaluation of the efficacy of Fluorescein, Rose Bengal, Lissamine Green, and a new dye mixture for ocular surface staining," Eye Contact Lens, Jan. 2008;34(1) 61-64. Jan. 1, 2008 (Jan. 1, 2008), XP055224976, Retrieved from the Internet: URL:http://www.ncbi.nlm.nih.gov/pubmed/181 80687 [retrieved on Nov. 2, 2015] * abstract * (1 page).
Lins, et al., "Enhancement of Antimicrobial Action of Photodynamic Therapy in the Presence of Hydrogen Peroxide", in Microbial Pathogens and Strategies for Combating Them: Science, Technology and Education, Edition: Microbiology Book Series #4, Editor: A. Mendez-Vilas, pp. 367-371 (2013) (acquired from:; https://www.researchgate.net/publication/283644315_Enhancement_of_Antimicrobial_Action_of_Photodynamic_Therapy_in_the_Presence_of_Hydrogen_Peroxide).
McCullach, et al., "Photosensitized destruction of *Chlorella vulgaris* by Methylene Blue or Nuclear Fast Red combined with hydrogen peroxide under visible light irradiation," Environmental Science and Technology, 40(7):2421-2425 (2006).
Meisel, et al., "Photodynamic therapy for periodontal diseases: state of the art," Journal of Photochemistry and Photobiology B: Biology, 79:159-170 (2005).
Mintel, "Gel Blush," http://gnpd.com; Jun. 2009 (4 pages).
Mintel, "Gold Bear Gums," http://gnpd.com, Feb. 2008 (3 pages).
Mintel, "Teens Braces Cleaner," http://gnpd.com, Jan. 2004 (2 pages).
Mintel, "Velvet Gloss Lip Pencil," http://gnpd.com; Feb. 2011 (4 pages).
Mintel, "Active Plus Deep Cleaning Tablets," Database GNPD [Online], May 2007, XP002769877, Database accession No. 707777 *Ingredients*.
Mintel, "Effervescent Tablets," Database GNPD [Online] May 2009, XP002769876, Database accession No. 1089966 *Ingredients*.
Mintel, "Photodynamic therapy SPF 30" XP002775115. Database accession No. 1442681, pp. 1.2.3.5 (Nov. 30, 2010).
Montenegro, et al., "Model studies on the photosensitized isomerization of bixin," Journal of Agriculture and Food Chemistry, 52(2): 367-73 (2004).
Nolan et al., "The efficacy of topical hyaluronic acid in the management of oral lichen planus," Journal of Oral Pathology and Medicine, 38(3):299-303 (2006).
Olympus America Inc., "Special characteristics of common biological stains," http://micro.magnet.fsu.edu/primer/photomicrography/bwstainchart.html, Apr. 30, 2000 (3 pages).
PCT International Preliminary Report on Patentability and Written Opinion for International Application No. PCT/CA2013/000787, dated Nov. 27, 2013 (9 pages).
PCT International Search Report and Written Opinion for International Application No. PCT/CA2011/050261, dated Aug. 4, 2011 (6 pages).
PCT International Search Report and Written Opinion for International Application No. PCT/CA2012/050177, dated Jun. 28, 2012 (8 pages).
PCT International Search Report and Written Opinion for International Application No. PCT/CA2013/000786, dated Jan. 8, 2014 (16 pages).
PCT International Search Report and Written Opinion for International Application No. PCT/CA2014/000161, dated May 30, 2014 (12 pages).
PCT International Search Report and Written Opinion for International Application No. PCT/CA2015/000407, dated Sep. 23, 2015 (13 pages).
PCT International Search Report and Written Opinion for International Application No. PCT/GR2007/000006, dated Oct. 12, 2007 (8 pages).
PCT International Search Report and Written Opinion for International Application No. PCT/IB2006/004034, dated Sep. 20, 2007 (13 pages).
PCT International Search Report Corrected for International Application No. PCT/CA2014/000261, dated Jul. 23, 2014 (7 pages).
PCT International Search Report for International Application No. PCT/CA2009/001615, dated Feb. 9, 2010 (9 pages).
PCT International Search Report for International Application No. PCT/CA2010/001134, dated Oct. 8, 2010 (3 pages).
PCT International Search Report for International Application No. PCT/CA2013/000395, dated Jul. 15, 2013 (12 Pages).
PCT International Search Report for International Application No. PCT/CA2014/000536, dated Oct. 16, 2014 (7 pages).
Publication date of following document established by Internet Archive Wayback Machine (3 pages) <URL: <http://web.archive.org/web/20090208211504/http://en.wikipedia.org/wiki/Eosin Aug. 2, 2009.
Resources: Fluorochrome absorption emission wavelengths, [Online] XP002449595 Retrieved from the Internet: URL: http://www.sciencegateway.org/resource s/fae1.htm>[retrieved on Sep. 6, 2007] see p. 2: Rhodamine WT emission nm 555 p. 2 (12 pages).
Roy, et al., "Dermal wound healing is subject to redox control," Molecular Therapy, 13(1):211-220 (2006).
Sezer, et al., "Topical drug delivery using chitosan nano- and microparticles," Expert Opinion in Drug Delivery, Informa UK, 9(9):1129-1146 (2012).
Slyusareva, et al. "Spectral and Photophysical Properties of Flourone Dyes in Bio-Related Films and Methanol", Journal of Photochemistry and Photobiology A; Chemistry 208 (2009), pp. 131-140.
Steinberg, et al., "Genetic and physiological effects of noncoherent visible light combined with hydrogen peroxide on *Streptococcus mutans* in biofilm," Antimicrobial Agents and Chemotherapy, 52(7):2626-2631 (2008).

(56) References Cited

OTHER PUBLICATIONS

Subba, et al, "Photocatalytic transformation of dyes and by-products in the presence of hydrogen peroxide," Environmental Technology, 24(8):1025-1030 (2003).
Sun, "Lasers and light amplification in dentistry," retrieved online at http://www.sundds.comllaser/, downloaded Jun. 23, 2005 (14 pages).
Tao, et al, "Gastrointestinal Patch Systems for Oral Drug Delivery", Drug Discovery Today, vol. 10, No. 13, Jul. 2005, pp. 909-915.
Thompson, et al., "Fluorescence polarization standards for high-throughput screening and imaging," Bio Techniques, 32(2002) (5 pages).
Tsuboi et al., "Photoluminescence Properties of Fluorone Dyes in Bio-Related Films at Low Temperatures" Journal of Photochemistry and Photobiology A; Chemistry; 222 (2011) pp. 336-342.
Samson et al. "Wound-Healing Technologies: Low-Level Laser and Vacuum-Assited Closure", Evidence Report/Technology Assessment 2004, 111, pp. 1-97 https://www.ncbi.nlm.nih.gov/books/NBK37464/toc/?report=reader.

\* cited by examiner

TISSUE FILLER COMPOSITIONS AND METHODS OF USE

CROSS-REFERENCE TO RELATED APPLICATIONS

This application is a national stage application under 35 U.S.C. § 371 of International Application No. PCT/CA2015/050261, filed Apr. 1, 2015, which claims the benefit of and priority to U.S. provisional patent application No. 61/973,659; filed Apr. 1, 2014, the content of which is herein incorporated in its entirety by reference. International Application PCT/US2009/059126 was published under PCT Article 21(2) in English.

FIELD OF TECHNOLOGY

The present disclosure generally relates to tissue filler compositions and methods of use. Specifically, but not exclusively, the present disclosure relates to tissue filler compositions which can be injected or implanted into soft tissues.

BACKGROUND OF THE DISCLOSURE

Tissue fillers are used in the medical and cosmetic fields for tissue augmentation, regeneration or re-shaping. In the cosmetic field, tissue fillers are known as dermal fillers and are injectable materials which can improve the appearance of skin by filling of wrinkles and folds, replacing lost tissue, or by facial contouring such as re-shaping the cheeks, chin or jaw. Tissue fillers are also used for treating scars by temporarily elevating a depressed scar.

It is an object of the present disclosure to provide new and improved tissue filler compositions and methods useful in medical and cosmetic fields.

SUMMARY OF SOME EMBODIMENTS OF THE PRESENT DISCLOSURE

According to various aspects, the present disclosure provides compositions and methods useful as tissue filler for medical and cosmetic indications.

According to various aspects, the present disclosure relates to a method for stimulating collagen synthesis comprising: administering a composition to an area to be treated within a soft tissue, wherein the composition comprises a tissue filler medium and a fluorophore; illuminating the area with light having a wavelength which can be absorbed by the fluorophore; wherein the method stimulates collagen synthesis in the area.

According to various aspects, the present disclosure relates to a method for cosmetic enhancement of soft tissue comprising: intradermally or subdermally administering a composition to an area to be treated, wherein the composition comprises a tissue filler medium and a fluorophore; illuminating the area with light having a wavelength which can be absorbed by the fluorophore; wherein the method stimulates collagen synthesis in the area to cosmetically enhance the soft tissue.

According to various aspects, the present disclosure relates to a method for skin rejuvenation comprising: intradermally or subdermally administering a composition to an area to be treated, wherein the composition comprises a tissue filler medium and a fluorophore; illuminating the area with light having a wavelength which can be absorbed by the fluorophore; wherein the method stimulates collagen synthesis in the area to cosmetically rejuvenate the skin.

According to various aspects, the present disclosure relates to a method for inhibiting or treating scarring, the method comprising: administering a composition to an area to be treated within or around a scar or a wound, wherein the composition comprises a tissue filler medium and a fluorophore; illuminating the area with light having a wavelength which can be absorbed by the fluorophore; wherein the method stimulates collagen synthesis in the area to prevent or reduce scar formation.

According to various aspects, the present disclosure relates to a method for promoting wound healing, the method comprising: administering a composition to an area to be treated within a wound, wherein the composition comprises a tissue filler medium and a fluorophore; illuminating the area with light having a wavelength which can be absorbed by the fluorophore; wherein the method stimulates wound healing in the area.

By means of certain embodiments of the present disclosure, light emitted by the fluorophore can induce or stimulate collagen synthesis in the soft tissue around the composition where there otherwise would be no collagen synthesis or where the collagen synthesis would be minimal. For example, the collagen synthesis induced by the fluorophore may be in addition to any collagen synthesis inherently induced by the tissue filler medium by mechanical means (e.g. when the tissue filler medium comprises hyaluronic acid) or by a foreign body response (e.g. when the tissue filler medium is a nonbiodegradable material). When the fluorophore is activated to emit fluorescent or phosphorescent light, the surrounding soft tissues are illuminated with a broader spectrum of light than if illuminated from outside the dermis or from a single light source. Also, the surrounding soft tissues may be illuminated with shorter wavelengths of light than those able to reach those soft tissues transdermally. In this way, a more efficient and wavelength specific illumination of the soft tissues, such as dermal/epidermal/subdermal layers can be achieved which may lead to a therapeutic or cosmetic effect.

In certain embodiments, the area to be treated is soft tissue. The area to be treated may be on any part of the body such as on a face, neck, ears, breasts, buttocks, arms, armpits, hands, genitalia, legs or feet of a human subject. In certain embodiments, the area to be treated is in or around a scar. The scar may be a post-surgical scar. The scar can be an old or a fresh scar. In certain embodiments, the area to be treated is in or around a wound. The wound may be an acute or a chronic wound, including burns. In certain embodiments, the area to be treated includes stretch marks. The area to be treated may be in or around a stretch mark.

In certain embodiments, the administering of the composition is by injection. The injection can be performed using a needle. The needle can have a gauge of 27 G to 40 G, typically 30 G or 32 G. The administering by injection can be a continuous injection, known as linear threading, or serial punctures to deposit microdroplets. In certain other embodiments, the administering of the composition is by implantation.

In certain embodiments, the composition is a cohesive gel. The composition may be a hydrated gel. The composition may be transparent or translucent. In certain embodiments, the tissue filler medium is a cohesive gel. The tissue filler medium may be a hydrated gel. The tissue filler medium may be transparent or translucent.

In certain embodiments, the tissue filler medium retains the fluorophore within the composition during administering of the composition, and at least during a portion of the illumination. Alternatively, in certain embodiments, the tissue filler medium/composition may allow the fluorophore to leach from the composition/tissue filler medium after administering to the tissue.

In certain embodiments, the tissue filler medium is biodegradable. The tissue filler medium may comprise any biodegradable and biocompatible material such as hyaluronic acid (HA), collagen, poly-L-lactic acid. Complete biodegradation may occur in about 3-18 months. The fluorophore may or may not affect the biodegradation rate of the tissue filler medium.

In certain embodiments, the tissue filler medium comprises cross-linked hyaluronic acid (cross-linked HA). The cross-linked hyaluronic acid may be about 0.1% to about 2%, about 2% to about 30%, about 2% to about 25%, about 2% to about 20%, about 2% to about 15%, about 2% to about 10%, about 2% to about 5%, 4% to about 30%, about 4% to about 25%, about 4% to about 20%, about 4% to about 15%, about 4% to about 10%, about 4% to about 5%, of the composition. In certain embodiments, the cross-linked hyaluronic acid is in particulate form. The particles may be hydrated. The particles may be cohesive. In certain embodiments, the fluorophore is within the cross-linked hyaluronic acid particle.

In certain embodiments, the composition further comprises an injectable medium supporting the particles. The injectable medium may be a fluid. The injectable medium may be less viscous and/or less cohesive than the particles. For example, the particles may be cohesive and the injectable medium non-cohesive. The fluorophore may be in the injectable medium or the particles, or both. In certain embodiments, the injectable medium comprises hyaluronic acid which is non-cross linked or relatively less cross-linked than the cross-linked hyaluronic acid particles.

In certain embodiments, the composition further comprises light reflecting particles. The light reflecting particles may be a glass or silicon dioxide.

In certain embodiments, the fluorophore is a hydrophilic chromophore. The fluorophore may be water soluble. In certain embodiments, the fluorophore is not in a liposomal form in the composition. In certain embodiments, the fluorophore can be activated by light having a wavelength in the visible range. In certain embodiments, the fluorophore does not absorb light in the UV range of the electromagnetic spectrum. In certain embodiments, when activated, the fluorophore can emit light having a wavelength in the visible range. The emitted light can be within one or more of the violet, blue, green, yellow, orange or red portions of the electromagnetic spectrum. Alternatively, the fluorophore can emit in the infrared range. In certain embodiments, the fluorophore can be photobleached after illumination of the area. In certain embodiments, the fluorophore may be photobleached after 5, 10, 15, 20, 25, 30, 35, 40, 45, 50, 55, 60 or 65 minutes of illumination. The illumination may be continuous or pulsed. The illumination may comprise re-illumination of the composition or the area after a few hours or days. In certain embodiments, by means of the photobleaching, photosensitivity is reduced or avoided. In certain embodiments, the fluorophore is not a photosensitizing agent requiring to be metabolized. For example, in certain embodiments, the fluorophore is not porphyrin, porphyrinogen, hematoporphyrin, pheophorbide, chlorin, bacteriochlorin, iso-bacteriochlorin and dihydro- and tetrahydro-tetrapyrroles. In certain embodiments, the fluorophore does not bind to native cells or cellular structures. In certain embodiments, the area is illuminated at the same time as or immediately after intradermal or subdermal administration. In other words, there is no incubation period between administering of the composition and illumination.

In certain embodiments, the illumination is for a time sufficient to activate the fluorophore. In certain embodiments, the illumination is for a time sufficient to photobleach the fluorophore. In certain embodiments, the illumination is for 1-30 seconds, 15-45 seconds, 30-60 seconds, 0.75-1.5 minutes, 1-2 minutes, 1.5-2.5 minutes, 2-3 minutes, 2.5-3.5 minutes, 3-4 minutes, 3.5-4.5 minutes, 4-5 minutes, 5-10 minutes, 10-15 minutes, 15-20 minutes, 20-25 minutes, or 25-30 minutes. The treatment time may range up to about 90 minutes, about 80 minutes, about 70 minutes, about 60 minutes, about 50 minutes, about 40 minutes or about 30 minutes.

In certain embodiments, the composition is illuminated by a light source positioned external to the dermis. In other words, illumination is transdermally.

In certain embodiments, intradermally or subdermally administration provides a track of HA-stimulated cells from the external surface to the dermis, thereby creating a light duct from the light source to the intradermal or subdermal in order to activate the composition.

In certain embodiments, the method further comprises applying a topical composition over the treatment area, wherein the topical composition comprises a fluorophore. The fluorescent compound may have an emission spectrum which can activate the fluorophore in the intradermal/subdermal composition. In this way a deeper illumination of soft tissues may be obtained. In certain embodiments, the topical composition is applied prior to light illumination.

According to various aspects, the present disclosure relates to a method for skin rejuvenation comprising: intradermally or subdermally administering a composition to an area to be treated, wherein the composition comprises a tissue filler medium and a fluorophore; topically applying a biophotonic composition to the skin above the area to be treated; and illuminating the topical biophotonic composition with light having a wavelength which can be absorbed by a chromophore in the topical biophotonic composition to cause the chromophore to emit light; wherein the fluorophore can absorb the emitted light from the topical biophotonic composition, wherein the method stimulates collagen synthesis in the area to cosmetically rejuvenate the skin. In certain embodiments, the composition is injectable and can be injected through a 23-40 gauge needle. In certain embodiments, the composition is injected under a wrinkle or a fold or a scar to provide an immediate lift to the defect. Illumination of the composition may then stimulate collagen synthesis around the injected composition to provide further skin rejuvenation.

From another aspect there is provided a tissue filler composition comprising: a tissue filler medium; and a fluorophore; wherein the composition is suitable for injection or implantation into a human.

In certain embodiments, the composition is a cohesive gel. The composition may be a hydrated gel. The composition may be transparent or translucent.

In certain embodiments, the tissue filler medium retains the fluorophore within the composition during administering of the composition, and at least during a portion of the illumination. Alternatively, the fluorophore may leach from the tissue filler medium after administering to the tissue.

In certain embodiments, the tissue filler medium is biodegradable. The tissue filler medium may comprise any biodegradable and biocompatible material such as hyaluronic acid, collagen, poly-L-lactic acid. Complete biodegradation may occur in about 3-18 months. The fluorophore may or may not affect the biodegradation rate of the tissue filler medium.

In certain embodiments, the tissue filler medium comprises cross-linked hyaluronic acid. The cross-linked hyaluronic acid may be about 0.1 to about 2%, about 2 to about 30%, about 2 to about 25%, about 2 to about 20%, about 2 to about 15%, about 2 to about 10%, about 2 to about 5%, 4 to about 30%, about 4 to about 25%, about 4 to about 20%, about 4 to about 15%, about 4 to about 10%, about 4 to about 5%, of the composition. In certain embodiments, the cross-linked hyaluronic acid is in particulate form. The particles may be hydrated. The particles may be cohesive. In certain embodiments, the fluorophore is within the cross-linked hyaluronic acid particle.

In certain embodiments, the composition further comprises an injectable medium supporting the particles. The injectable medium may be a fluid. The injectable medium may be less viscous and/or less cohesive than the particles. For example, the particles may be cohesive and the injectable medium non-cohesive. The fluorophore may be in the injectable medium or the particles, or both. In certain embodiments, the injectable medium comprises hyaluronic acid which is non-cross linked or relatively less cross-linked than the cross-linked hyaluronic acid particles.

In certain embodiments, the composition further comprises light reflecting particles. The light reflecting particles may be a glass or silicon dioxide.

In certain embodiments, the fluorophore is a hydrophilic chromophore. The fluorophore may be water soluble. In certain embodiments, the fluorophore is not in a liposomal form in the composition.

In certain embodiments, the fluorophore can be activated by light having a wavelength in the visible range. In certain embodiments, the fluorophore does not absorb light in the UV range of the electromagnetic spectrum. In certain embodiments, when activated, the fluorophore can emit light having a wavelength in the visible range. The emitted light can be within one or more of the violet, blue, green, yellow, orange or red portions of the electromagnetic spectrum. Alternatively, the fluorophore can emit in the infrared range.

In certain embodiments, the fluorophore can be photobleached after illumination of the area. In certain embodiments, the fluorophore may be photobleached after 5, 10, 15, 20, 25, 30, 35, 40, 45, 50, 55, 60 or 65 minutes of illumination. In certain embodiments, the fluorophore may be photobleached after 1-30 seconds, 15-45 seconds, 30-60 seconds, 0.75-1.5 minutes, 1-2 minutes, 1.5-2.5 minutes, 2-3 minutes, 2.5-3.5 minutes, 3-4 minutes, 3.5-4.5 minutes, 4-5 minutes, 5-10 minutes, 10-15 minutes, 15-20 minutes, 20-25 minutes, or 25-30 minutes. The treatment time may range up to about 90 minutes, about 80 minutes, about 70 minutes, about 60 minutes, about 50 minutes, about 40 minutes or about 30 minutes. The illumination may be continuous or pulsed. The illumination may comprise re-illumination of the composition or the area after a few hours or days.

In certain embodiments, the fluorophore is not a photosensitizing agent requiring to be metabolized. For example, in certain embodiments, the fluorophore is not porphyrin, porphyrinogen, hematoporphyrin, pheophorbide, chlorin, bacteriochlorin, iso-bacteriochlorin and dihydro- and tetra-hydro-tetrapyrroles. In certain embodiments, the fluorophore does not bind to native cells, cancer cells or other cellular structures.

In certain embodiments the composition does not include glucosamine. In certain embodiments where the composition comprises hyaluronic acid, the composition does not include glucosamine. In certain embodiments, the composition does not include a source of oxygen such as peroxide. In certain embodiments, the composition does not include hydrophobic fluorophores. In certain embodiments, the composition is not photopolymerizable. In certain embodiments, the composition does not include a monomer. In certain embodiments, the composition does not include hyaluronic acid with functionalized chains. In certain embodiments of any of the foregoing or following, the composition does not include one or more (e.g., 1, 2 or 3) of triethanolamine (TEA), N-vinyl-2-pyrrolidone (NVP), or N-vinyl caprolactam (NVC). In certain embodiments, the composition does not include any of triethanolamine (TEA), N-vinyl-2-pyrrolidone (NVP), or N-vinyl caprolactam (NVC).

In certain embodiments of any of the foregoing or following, the composition is a sterile composition. In certain embodiments, the composition can be sterilized by heat and/or pressure, such as using an autoclave. In certain embodiments, the composition can be sterilized by gamma irradiation. In certain embodiments of any of the above aspects, the subdermally or intradermally placed composition can provide an immediate 'lifting' which may be due in part to its cohesive or viscoelastic properties. This is beneficial in smoothing of lines and folds on skin to provide an appearance of skin rejuvenation. In certain embodiments, the 'lifting' effect of the subdermally or intradermally placed composition diminishes over time as the tissue filler medium degrades, is compressed and/or is dispersed. Therefore, by means of certain embodiments of the present disclosure, a prolonged skin rejuvenation effect can be obtained by providing an immediate lifting effect to the skin which gradually diminishes with time, and at the same time synthesis of new collagen at or around the intradermal or subdermal composition which increases over time. As the tissue filler degradation and the collagen synthesis dovetail into one another, a substantially continuous skin rejuvenation effect may be achieved.

In certain embodiments, the new collagen on or around the intracorporeal composition substantially matches the extracellular matrix in terms of collagen type, collagen mechanical properties and collagen fibrillar orientation. This is unlike existing degradable tissue filler media which either induce collagen synthesis but do not provide a lifting effect (e.g. fillers based on poly-L-lactic acid), or which provide a lifting effect but which do not induce significant collagen synthesis (e.g. hyaluronic acid based dermal fillers), or which provide a lifting effect and induce collagen synthesis having different properties to the extracellular matrix (e.g. permanent dermal fillers).

According to various aspects, the present disclosure relates to the use of a composition as described herein, for stimulating collagen synthesis within soft tissues. From another aspect, there is provided use of a composition as described herein, for cosmetic enhancement of soft tissues. From another aspect, there is provided use of a composition as described herein, for inhibiting or treating scarring. From another aspect, there is provided use of a composition as described herein, for skin rejuvenation. From another aspect, there is provided use of a composition as described herein, together with a topical biophotonic composition for skin rejuvenation.

According to various aspects, the present disclosure relates to the use of a composition comprising a tissue filler medium and a fluorophore in a method for stimulating collagen synthesis, wherein the method comprises a step of administration of the composition to an area to be treated within a soft tissue, and a step illumination of the area with light having a wavelength which can be absorbed by the fluorophore; and wherein the method stimulates collagen synthesis in the area.

According to various aspects, the present disclosure relates to the use of a composition comprising a tissue filler medium and a fluorophore in a method for cosmetic enhancement of soft tissue, wherein the method comprises a step of administration of the composition to an area to be treated within a soft tissue, and a step illumination of the area with light having a wavelength which can be absorbed by the fluorophore; and wherein the method cosmetically enhances the soft tissue.

According to various aspects, the present disclosure relates to the use of a composition comprising a tissue filler medium and a fluorophore in a method for inhibiting or treating scarring, wherein the method comprises a step of administration of the composition to an area to be treated within a soft tissue, and a step illumination of the area with light having a wavelength which can be absorbed by the fluorophore; and wherein the method cosmetically inhibits or treats scarring.

According to various aspects, the present disclosure relates a tissue filler composition comprising more than one tissue filler medium, wherein the composition is suitable for injection or implantation into a human.

According to various aspects, the present disclosure relates a method for stimulating collagen synthesis comprising: administering a first composition to an area to be treated within a soft tissue, wherein the first composition comprises a tissue filler medium; administering on a surface over the area to be treated a second composition comprising a fluorophore; and illuminating the area with light having a wavelength which can be absorbed by the fluorophore; wherein the method stimulates collagen synthesis in the area.

DETAILED DESCRIPTION

Figure 1:
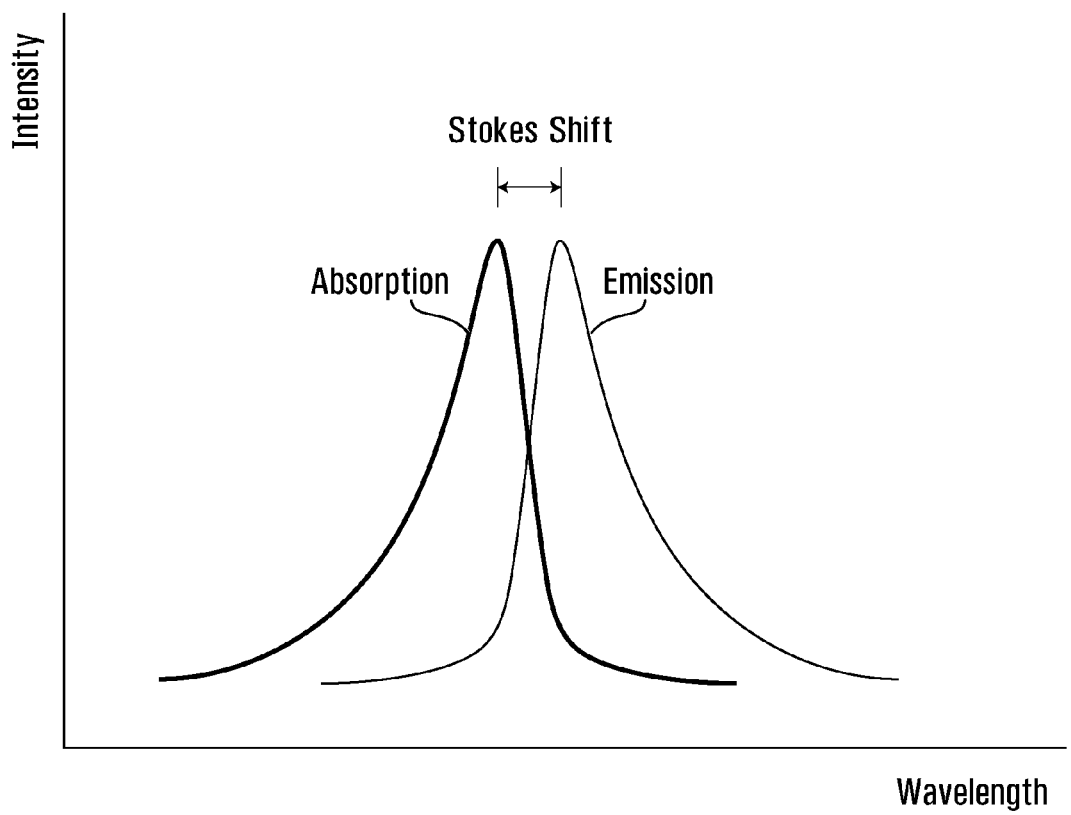
FIG. 1 is a graph illustrating the Stokes' shift.

The present disclosure provides compositions which can be used as tissue fillers and which are biophotonic. The tissue filler compositions of the present disclosure include a photoactive exogenous chromophore together with a tissue filler medium, and may be injectable or implantable or deliverable to soft tissues in any other way. The present disclosure also provides methods useful for stimulating collagen synthesis; cosmetic enhancement of soft tissue such as soft tissue augmentation, rejuvenation or re-shaping; inhibition or treatment of scars; or promoting wound healing, using such tissue filler compositions.

Before continuing to describe the present disclosure in further detail, it is to be understood that this disclosure is not limited to specific compositions or process steps, as such may vary.

It must be noted that, as used in this specification and the appended claims, the singular form "a", "an" and "the" include plural referents unless the context clearly dictates otherwise.

As used herein, the term "about" in the context of a given value or range refers to a value or range that is within 20%, preferably within 10%, and more preferably within 5% of the given value or range.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

"Biophotonic" means the generation, manipulation, detection and application of photons in a biologically relevant context. In other words, biophotonic compositions exert their physiological effects primarily due to the generation and manipulation of photons. Biophotonic compositions may also generate reactive oxygen species. "Biophotonic composition" is a composition as described herein that may be activated by light to produce photons and/or reactive oxygen species for biologically relevant applications.

Terms "chromophore", "photoactivating agent" and "photoactivator" are used herein interchangeably. A chromophore means a chemical compound, when contacted by light irradiation, is capable of absorbing the light. The chromophore readily undergoes photoexcitation and can then transfer its energy to other molecules and/or emit it as light. The chromophore may be a synthetic chromophore or a naturally occurring chromophore.

"Fluorophore" as used herein means a chromophore which can emit light upon light excitation e.g. by fluorescence, phosphorescence or any other means.

"Tissue filler" when used herein means a material that is suitable for, or generally used for, tissue augmentation, regeneration or re-shaping such as those suitable for use or used in the dermis area such as dermal fillers, or those suitable for use or used in any other soft tissue for example as a scaffold or a delivery material. Tissue fillers include biodegradable and non-biodegradable materials, as well as natural and synthetic materials, including hydrogels. Tissue fillers can be administered by any means such as by injection or implantation. Tissue fillers can be administered to any soft tissue site such as subcutaneous, hypodermic and/or intradermal. "Dermal filler" when used herein means a material which can be used in the dermis area, such as below the epidermis and/or above or below the hypodermis, such as for tissue augmentation, regeneration or re-shaping. Dermal fillers can be delivered by hypodermic and/or intradermal injection, or by any other means such as implantation.

As used herein, the expression "soft tissue" refers to tissues that connect, support, or surround other structures and organs of the body, not being bone. Soft tissue includes tendons, ligaments, fascia, skin, fibrous tissues, fat, and synovial membranes (which are connective tissue), and muscles, nerves and blood vessels (which are not connective tissue). It is sometimes defined by what it is not. Soft tissue has been defined as "nonepithelial, extraskeletal mesenchyme exclusive of the reticuloendothelial system and glia".

"Injectable" when used herein means a flowable material which may be drawn through or pushed through a needle by a syringe for injection into a soft tissue. Soft tissue includes tendons, ligaments, fascia, skin, dermis, fibrous tissues, fat, synovial membranes, muscles, nerves and blood vessels.

"Inhibiting or treating scarring" as used herein means preventing or minimizing scar formation, or reducing an existing scar. The scarring can be a result of any wound such as a burn or a surgical incision.

"Photobleaching" means the photochemical destruction of a chromophore.

The term "light" or "actinic light" is intended to mean light energy emitted from a specific light source (e.g., lamp, LED, laser) and capable of being absorbed by matter (e.g. the chromophore or photoactivator defined above). In a preferred embodiment, the light has a peak wavelength within the visible range of the electromagnetic spectrum, e.g. 360 nm to 760 nm.

"Wound" means an injury to any tissue, including for example, acute, subacute, delayed or difficult to heal wounds, and chronic wounds. Examples of wounds may include both open and closed wounds. Wounds include, for example, amputations, burns, incisions, excisions, lesions, lacerations, abrasions, puncture or penetrating wounds, surgical wounds, contusions, hematomas, crushing injuries, ulcers (such as for example pressure, venous, arterial or diabetic), wounds caused by periodontitis (inflammation of the periodontium).

"Skin rejuvenation" means the reducing, diminishing, retarding or reversing of one or more signs of skin aging or skin damage. Skin rejuvenation also means generally improving the cosmetic appearance of skin or cosmetic enhancement of skin. For instance, it includes increasing luminosity of the skin; reducing pore size; reducing fine lines or wrinkles; improving thin and transparent skin; improving firmness; improving plumpness; augmenting tissue loss or sagging skin due to loss of underlying fat or bone; improving dry skin (which might itch); reducing or reversing freckles, age spots, spider veins, or a blotchy complexion; improving rough and leathery skin; or improving fine wrinkles that disappear when stretched. According to the present disclosure, one or more of the above conditions may be improved or one or more of the above signs of aging may be reduced, diminished, retarded or even reversed by certain embodiments of the compositions, methods and uses of the present disclosure.

In some embodiments, the present disclosure provides biophotonic compositions which can be injected or implanted within soft tissue as tissue fillers. The present disclosure provides intracorporeal biophotonic compositions. Biophotonic compositions are compositions that are, in a broad sense, activated by light (e.g., photons) of specific wavelength. These compositions contain at least one exogenous chromophore which can be activated by light having an appropriate wavelength causing the chromophore to emit light. The activating and/or emitted light may have a therapeutic effect on its own. The activated chromophore and/or the light may also lead to the photochemical activation of other agents contained in the composition or at a treatment site. For example, in the presence of an oxygen-releasing agent, such an agent may be activated leading to the formation of oxygen radicals, such as singlet oxygen. The oxygen-releasing agent may be an internal source of oxygen such as blood.

In some aspects, the present disclosure provides biophotonic compositions comprising at least a first chromophore and a tissue filler medium. When a chromophore absorbs a photon of a certain wavelength, it becomes excited. This is an unstable condition and the molecule tries to return to the ground state, giving away the excess energy. For some chromophores, it is favorable to emit the excess energy as light when transforming back to the ground state. This process is called fluorescence and these chromophores are also known as "fluorophores". The peak wavelength of the emitted fluorescence is shifted towards longer wavelengths compared to the absorption wavelengths due to loss of energy in the conversion process. This is called the Stokes' shift and is illustrated in FIG. 1. In the proper environment (e.g., in a biophotonic composition) much of this energy is transferred to other components of the composition or to the treatment site directly.

Figure 2:
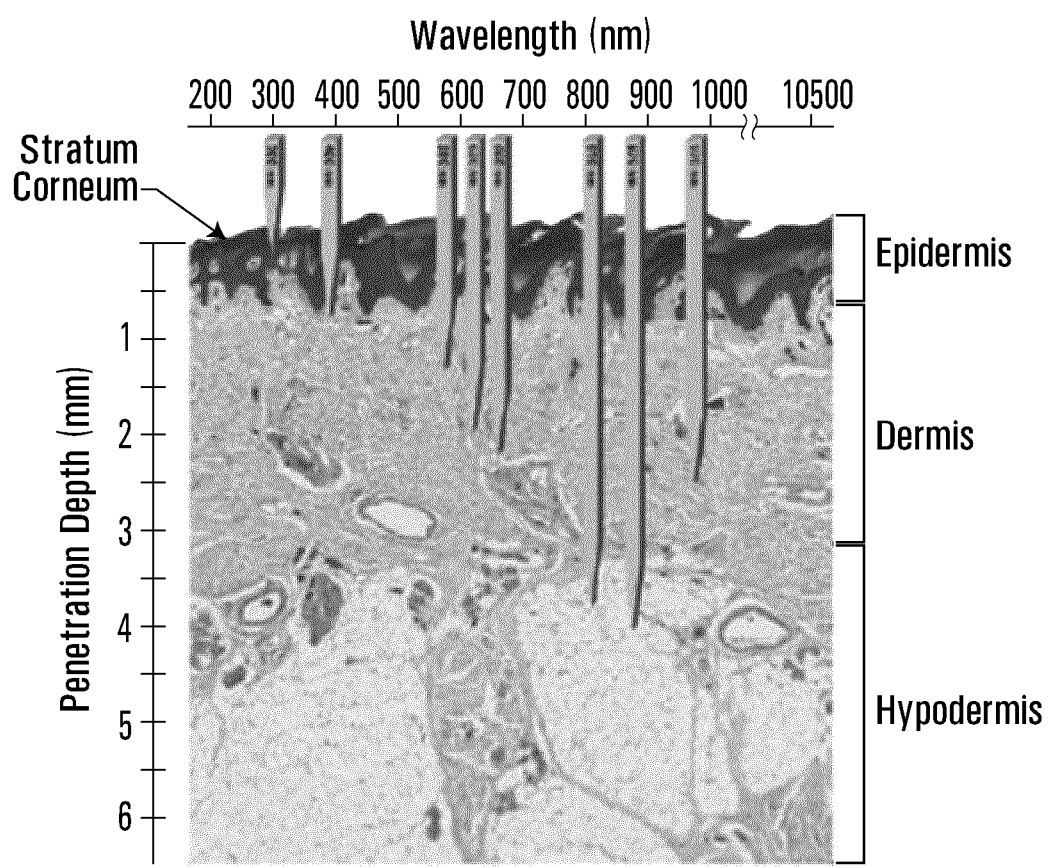
FIG. 2 is a picture depicting the absorption of light in the various layers of the skin (Samson et al. Evidence Report/Technology Assessment 2004, 111, pages 1-97).

Without being bound to theory, it is thought that fluorescent light emitted by photoactivated chromophores may have therapeutic properties due to its femto-, pico- or nano-second emission properties which may be recognized by biological cells and tissues, leading to favorable biomodulation. Furthermore, the emitted fluorescent light has a longer wavelength and hence a deeper penetration into the tissue than the activating light (FIG. 2). Irradiating intradermal, subdermal or other soft tissue with such a broad range of wavelengths, including in some embodiments the activating light which passes through the composition, may have different and complementary effects on the cells and tissues.

In certain embodiments, the tissues surrounding the biophotonic composition will be illuminated with wavelengths of light which would not normally reach those soft tissue sites if illuminated transdermally due to the short wavelengths and the depth from the skin. In certain embodiments, this may lead to a therapeutic or cosmetic benefit to the soft tissues surrounding the biophotonic composition in use, such as stimulation of collagen production. This may be in addition to any physical filling and lifting effects of a typical tissue filler, as well as in addition to any collagen production due induced by locally applied stresses from the tissue filler. Furthermore, the collagen which is produced may more closely match that of the extracellular collagen matrix of the area being treated compared to fibrous collagen formation through foreign body response seen with some existing tissue fillers. That is the type of collagen, the mechanical properties of the collagen, and collagen fibrillar direction will more closely match that of native collagen.

In some instances, the biophotonic compositions of the present disclosure may be capable of triggering changes in cell signalling as so to produce an increase in collagen deposition through fibroblast stimulation and thereby modifying the extracellular matrix locally.

The biophotonic compositions of the present disclosure may be substantially transparent/translucent and/or have high light transmittance in order to permit light dissipation into and through the composition. In this way, the area of tissue around the composition can be treated both with the fluorescent light emitted by the composition and the light irradiating the composition to activate it. The % transmittance of the biophotonic composition can be measured in the range of wavelengths from 250 nm to 800 nm using, for example, a Perkin-Elmer Lambda 9500 series UV-visible spectrophotometer. In some embodiments, transmittance within the visible range is measured and averaged. In some other embodiments, transmittance of the biophotonic material is measured with the chromophore omitted. In some embodiments, transmittance of the compositions disclosed herein is measured at 460 nm. As transmittance is dependent upon thickness, the thickness of each sample can be measured with calipers prior to loading in the spectrophotometer. Transmittance values can be normalized to a thickness of 100 μm (or any thickness) according to the following formula:

$$F_{T\text{-}corr}(\lambda,t_2)=[e^{-\alpha_t(\lambda)t_1}]^{t2/t1}=[F_{T\text{-}corr}(\lambda,t_1)]^{t2/t1},$$

where $t_1$=actual specimen thickness, $t_2$=thickness to which transmittance measurements can be normalized. In the art, transmittance measurements are usually normalized to 1 cm. In some embodiments, the biophotonic composition has a transmittance that exceeds about 15%, about 20%, about 30%, about 40%, about 50%, about 55%, about 60%, about 65%, about 70%, about 75%, about 80%, or about 85% within the visible range. In some embodiments, the transmittance exceeds about 70%, about 86%, about 87%, about 88%, about 89%, about 90%, about 91%, about 92%, about 93%, about 94%, about 95%, about 96%, about 97%, about 98% or about 99% within the visible range of the electromagnetic spectrum (e.g. 400-700 nm).

The biophotonic compositions of the present disclosure are injectable or implantable, or deliverable intracorporeally to a soft tissue site by any other means.

These compositions may be described based on the components making up the composition. Additionally or alternatively, the compositions of the present disclosure have functional and structural properties and these properties may also be used to define and describe the compositions. Individual components of the composition of the present disclosure are detailed as below.

The compositions of the present disclosure comprise one or more chromophores, which can be considered exogenous, e.g., are not naturally present in skin or tissue. Suitable chromophores can be fluorophores or fluorochromes such as fluorescent dyes (or stains), although other dye groups or dyes (biological and histological dyes, food colorings, carotenoids, naturally occurring fluorescent and other dyes) can also be used. Suitable photoactivators can be those that are Generally Regarded As Safe (GRAS). Photoactivators which are not well tolerated by the skin or other tissues can be included in the biophotonic composition in an encapsulated, or chemically modified form.

In certain embodiments, the biophotonic composition of the present disclosure comprises a first chromophore which undergoes partial or complete photobleaching upon application of light. By photobleaching is meant a photochemical destruction of the chromophore which can generally be visualized as a loss of color. In some embodiments, the first chromophore absorbs at a wavelength in the range of the visible spectrum, such as at a wavelength of about 380-800 nm, about 380-700, about 400-700 or about 380-600 nm. In these embodiments, the first chromophore is not activated by UV light. In other embodiments, the first chromophore absorbs at a wavelength of about 200-800 nm, about 200-700 nm, about 200-600 nm or about 200-500 nm. In one embodiment, the first chromophore absorbs at a wavelength of about 200-600 nm. In some embodiments, the first chromophore absorbs light at a wavelength of about 200-300 nm, about 250-350 nm, about 300-400 nm, about 350-450 nm, about 400-500 nm, about 400-600 nm, about 450-650 nm, about 600-700 nm, about 650-750 nm or about 700-800 nm.

It will be appreciated by those skilled in the art that optical properties of a particular chromophore may vary depending on the chromophore's surrounding medium. Therefore, as used herein, a particular chromophore's absorption and/or emission wavelength (or spectrum) corresponds to the wavelengths (or spectrum) measured in a biophotonic composition of the present disclosure.

The biophotonic compositions disclosed herein may include at least one additional chromophore. Combining chromophores may increase photo-absorption by the combined dye molecules and enhance absorption and photobiomodulation selectivity. This creates multiple possibilities of generating new photosensitive, and/or selective chromophore mixtures.

Figure 3:
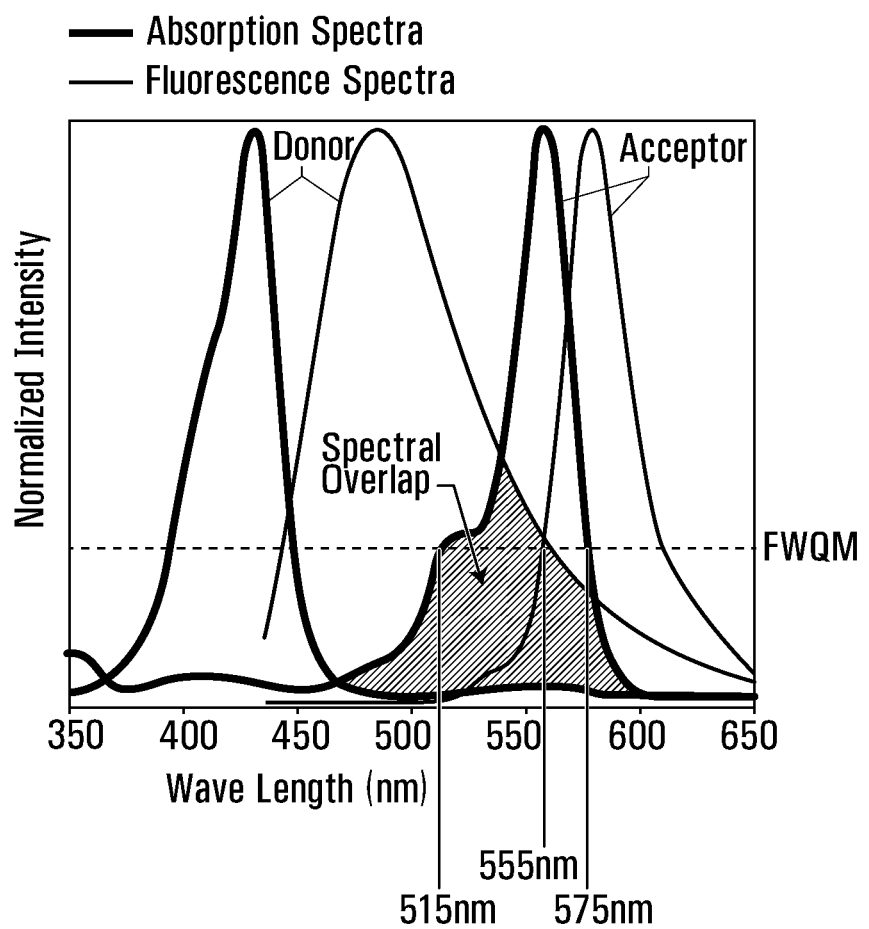
FIG. 3 is a graph illustrating the absorption and emission spectra of donor and acceptor chromophores. The spectral overlap between the absorption spectrum of the acceptor chromophore and the emission spectrum of the donor chromophore is also shown.
Figure 4:
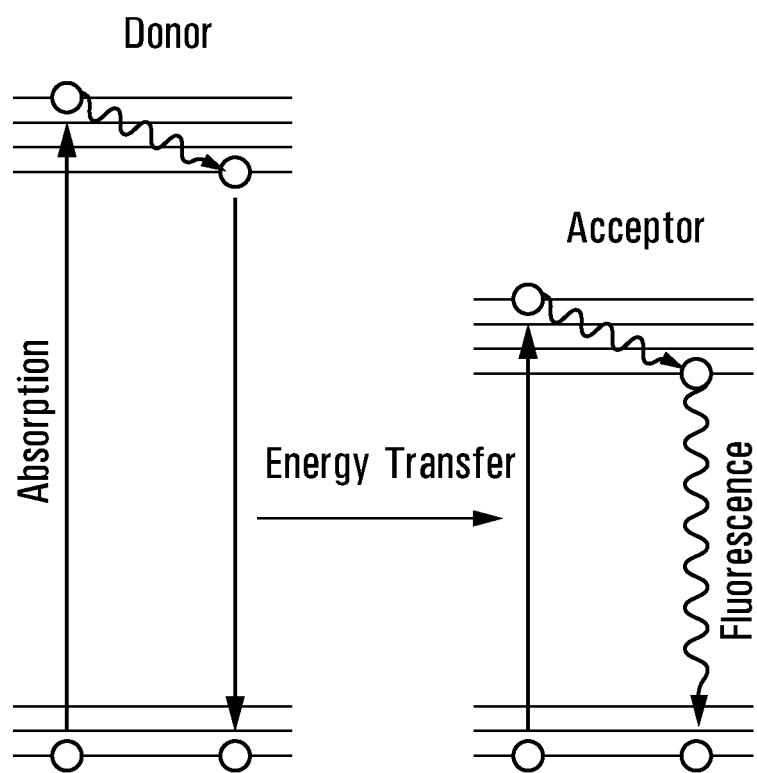
FIG. 4 is a schematic representation of a Jablonski diagram that illustrates the coupled transitions involved between a donor emission and acceptor absorbance.

When such multi-chromophore compositions are illuminated with light, energy transfer can occur between the chromophores. This process, known as resonance energy transfer, is a photophysical process through which an excited 'donor' chromophore (also referred to herein as first chromophore) transfers its excitation energy to an 'acceptor' chromophore (also referred to herein as second chromophore). The efficiency and directedness of resonance energy transfer depends on the spectral features of donor and acceptor chromophores. In particular, the flow of energy between chromophores is dependent on a spectral overlap reflecting the relative positioning and shapes of the absorption and emission spectra. For energy transfer to occur, the emission spectrum of the donor chromophore must overlap with the absorption spectrum of the acceptor chromophore (FIG. 3). Energy transfer manifests itself through decrease or quenching of the donor emission and a reduction of excited state lifetime accompanied also by an increase in acceptor emission intensity. FIG. 4 is a Jablonski diagram that illustrates the coupled transitions involved between a donor emission and acceptor absorbance. To enhance the energy transfer efficiency, the donor chromophore should have good abilities to absorb photons and emit photons. Furthermore, it is thought that the more overlap there is between the donor chromophores' emission spectra and the acceptor chromophore's absorption spectra, the better a donor chromophore can transfer energy to the acceptor chromophore.

In certain embodiments, the biophotonic composition of the present disclosure further comprises a second chromophore. In some embodiments, the first chromophore has an emission spectrum that overlaps at least about 80%, at least about 50%, at least about 40%, at least about 30%, at least about 20%, or at least about 10% with an absorption spectrum of the second chromophore. In one embodiment, the first chromophore has an emission spectrum that overlaps at least about 20% with an absorption spectrum of the second chromophore. In some embodiments, the first chromophore has an emission spectrum that overlaps at least about 1-10%, at least about 5-15%, at least about 10-20%, at least about 15-25%, at least about 20-30%, at least about 25-35%, at least about 30-40%, at least about 35-45%, at least about 50-60%, at least about 55-65% or at least about 60-70% with an absorption spectrum of the second chromophore.

% spectral overlap, as used herein, means the % overlap of a donor chromophore's emission wavelength range with an acceptor chromophore's absorption wavelength range, measured at spectral full width quarter maximum (FWQM). For example, FIG. 2 shows the normalized absorption and emission spectra of donor and acceptor chromophores. The spectral FWQM of the acceptor chromophore's absorption spectrum is from about 60 nm (515 nm to about 575 nm). The overlap of the donor chromophore's spectrum with the absorption spectrum of the acceptor chromophore is about 40 nm (from 515 nm to about 555 nm). Thus, the % overlap can be calculated as 40 nm/60 nm×100=66.6%.

In some embodiments, the second chromophore absorbs at a wavelength in the range of the visible spectrum. In certain embodiments, the second chromophore has an absorption wavelength that is relatively longer than that of the first chromophore within the range of about 50-250, about 25-150 or about 10-100 nm.

As discussed above, the application of light to the compositions of the present disclosure can result in a cascade of energy transfer between the chromophores. In certain embodiments, such a cascade of energy transfer provides emission of photons from inside the soft tissue that can travel deeper than if the photons were travelling transdermally. In some embodiments, such a cascade of energy transfer is not accompanied by concomitant generation of heat. In some other embodiments, the cascade of energy transfer does not result in tissue damage.

Optionally, when the biophotonic composition comprises a first and a second chromophore, the first chromophore is present in an amount of about 0.001-40% per weight of the composition, and the second chromophore is present in an amount of about 0.001-40% per weight of the composition. In certain embodiments, the total weight per weight of chromophore or combination of chromophores may be in the amount of about 0.001-40.001% per weight of the composition. In certain embodiments, the first chromophore is present in an amount of about 0.001-0.01%, about 0.001-0.05%, about 0.005-0.01%, about 0.01-1%, about 0.01-2%, about 0.05-1%, about 0.05-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40% per weight of the composition. In certain embodiments, the second chromophore is present in an amount of about 0.001-1%, about 0.001-2%, about 0.001-0.01%, about 0.01-0.1%, about 0.1-1.0%, about 1-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, 3 about 2.5-37.5%, or about 35-40% per weight of the composition. In certain embodiments, the total weight % per weight of chromophore or combination of chromophores may be in the amount of about 0.001-1%, about 0.01-1%, about 0.01-2%, about 0.05-2%, about 0.5-1%, about 0.5-2%, about 1-5%, about 2.5-7.5%, about 5-10%, about 7.5-12.5%, about 10-15%, about 12.5-17.5%, about 15-20%, about 17.5-22.5%, about 20-25%, about 22.5-27.5%, about 25-30%, about 27.5-32.5%, about 30-35%, about 32.5-37.5%, or about 35-40.05% per weight of the composition.

In some embodiments, the chromophore or chromophores are selected such that their emitted fluorescent light, on photoactivation, is within one or more of the blue, green, yellow, orange, red and infrared portions of the electromagnetic spectrum, for example having a peak wavelength within the range of about 450 nm to about 500 nm, 490 nm to about 800 nm, or about 470 nm to about 700 nm. In certain embodiments, the emitted fluorescent light has a peak power density of between 0.005 to about 10 mW/cm$^2$, or about 0.5 to about 5 mW/cm$^2$.

Suitable chromophores that may be used in the biophotonic compositions of the present disclosure include, but are not limited to the following:

Chlorophyll dyes—Exemplary chlorophyll dyes include but are not limited to chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Xanthene derivatives—Exemplary xanthene dyes include but are not limited to Eosin B (4',5'-dibromo,2',7'-dinitro-fluorescein, dianion); eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion) p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-fluorescein, dianion); eosin; eosin dicetylpyridinium chloride ion pair; erythrosin B (2',4',5',7'-tetraiodo-fluorescein, dianion); erythrosin; erythrosin dianion; erythiosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodofluorescein, dianion); pyronin G, pyronin J, pyronin Y; Rhodamine dyes such as rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Methylene blue dyes—Exemplary methylene blue derivatives include but are not limited to 1-methyl methylene blue; 1,9-dimethyl methylene blue; methylene blue; methylene blue (16 µM); methylene blue (14 µM); methylene violet; bromomethylene violet; 4-iodomethylene violet; 1,9-dimethyl-3-dimethyl-amino-7-diethyl-a-mino-phenothiazine; and 1,9-dimethyl-3-diethylamino-7-dibutyl-amino-phenothiazine.

Azo dyes—Exemplary azo (or diazo-) dyes include but are not limited to methyl violet, neutral red, para red (pigment red 1), amaranth (Azorubine S), Carmoisine (azorubine, food red 3, acid red 14), allura red AC (FD&C 40), tartrazine (FD&C Yellow 5), orange G (acid orange 10), Ponceau 4R (food red 7), methyl red (acid red 2), and murexide-ammonium purpurate.

In some aspects of the disclosure, the one or more chromophores of the biophotonic composition disclosed herein can be independently selected from any of Acid black 1, Acid blue 22, Acid blue 93, Acid fuchsin, Acid green, Acid green 1, Acid green 5, Acid magenta, Acid orange 10, Acid red 26, Acid red 29, Acid red 44, Acid red 51, Acid red 66, Acid red 87, Acid red 91, Acid red 92, Acid red 94, Acid red 101, Acid red 103, Acid roseine, Acid rubin, Acid violet 19, Acid yellow 1, Acid yellow 9, Acid yellow 23, Acid yellow 24, Acid yellow 36, Acid yellow 73, Acid yellow S, Acridine orange, Acriflavine, Alcian blue, Alcian yellow, Alcohol soluble eosin, Alizarin, Alizarin blue 2RC, Alizarin carmine, Alizarin cyanin BBS, Alizarol cyanin R, Alizarin red S, Alizarin purpurin, Aluminon, Amido black 10B, Amidoschwarz, Aniline blue WS, Anthracene blue SWR, Auramine O, Azocannine B, Azocarmine G, Azoic diazo 5, Azoic diazo 48, Azure A, Azure B, Azure C, Basic blue 8, Basic blue 9, Basic blue 12, Basic blue 15, Basic blue 17, Basic blue 20, Basic blue 26, Basic brown 1, Basic fuchsin, Basic green 4, Basic orange 14, Basic red 2 (Saffranin O), Basic red 5, Basic red 9, Basic violet 2, Basic violet 3, Basic violet 4, Basic violet 10, Basic violet 14, Basic yellow 1, Basic yellow 2, Biebrich scarlet, Bismarck brown Y, Brilliant crystal scarlet 6R, Calcium red, Carmine, Carminic acid (acid red 4), Celestine blue B, China blue, Cochineal, Coelestine blue, Chrome violet CG, Chromotrope 2R, Chromoxane cyanin R, Congo corinth, Congo red, Cotton blue, Cotton red, Croceine scarlet, Crocin, Crystal ponceau 6R, Crystal violet, Dahlia, Diamond green B, DiOC6, Direct blue 14, Direct blue 58, Direct red, Direct red 10, Direct red 28, Direct red 80, Direct yellow 7, Eosin B, Eosin Bluish, Eosin, Eosin Y, Eosin yellowish, Eosinol, Erie garnet B, Eriochrome cyanin R, Erythrosin B, Ethyl eosin, Ethyl green, Ethyl violet, Evans blue, Fast blue B, Fast green FCF, Fast red B, Fast yellow, Fluorescein, Food green 3, Gallein, Gallamine blue, Gallocyanin, Gentian violet, Haematein, Haematine, Haematoxylin, Helio fast rubin BBL, Helvetia blue, Hematein, Hematine, Hematoxylin, Hoffman's violet, Imperial red, Indocyanin green, Ingrain blue, Ingrain blue 1, Ingrain yellow 1, INT, Kermes, Kermesic acid, Kernechtrot, Lac, Laccaic acid, Lauth's violet, Light green, Lissamine green SF, Luxol fast blue, Magenta O, Magenta I, Magenta II, Magenta III, Malachite green, Manchester brown, Martius yellow, Merbromin, Mercurochrome, Metanil yellow, Methylene azure A, Methylene azure B, Methylene azure C, Methylene blue, Methyl blue, Methyl green, Methyl violet, Methyl violet 2B, Methyl violet 10B, Mordant blue 3, Mordant blue 10, Mordant blue 14, Mordant blue 23, Mordant blue 32, Mordant blue 45, Mordant red 3, Mordant red 11, Mordant violet 25, Mordant violet 39 Naphthol blue black, Naphthol green B, Naphthol yellow S, Natural black 1, Natural red, Natural red 3, Natural red 4, Natural red 8, Natural red 16, Natural red 25, Natural red 28, Natural yellow 6, NBT, Neutral red, New fuchsin, Niagara blue 3B, Night blue, Nile blue, Nile blue A, Nile blue oxazone, Nile blue sulphate, Nile red, Nitro BT, Nitro blue tetrazolium, Nuclear fast red, Oil red O, Orange G, Orcein, Pararosanilin, Phloxine B, phycobilins, Phycocyanins, Phycoerythrins. Phycoerythrincyanin (PEC), Phthalocyanines, Picric acid, Ponceau 2R, Ponceau 6R, Ponceau B, Ponceau de Xylidine, Ponceau S, Primula, Purpurin, Pyronin B, Pyronin G, Pyronin Y, Rhodamine B, Rosanilin, Rose bengal, Saffron, Safranin O, Scarlet R, Scarlet red, Scharlach R, Shellac, Sirius red F3B, Solochrome cyanin R, Soluble blue, Solvent black 3, Solvent blue 38, Solvent red 23, Solvent red 24, Solvent red 27, Solvent red 45, Solvent yellow 94, Spirit soluble eosin, Sudan III, Sudan IV, Sudan black B, Sulfur yellow S, Swiss blue, Tartrazine, Thioflavine S, Thioflavine T, Thionin, Toluidine blue, Toluyline red, Tropaeolin G, Trypaflavine, Trypan blue, Uranin, Victoria blue 4R, Victoria blue B, Victoria green B, Water blue I, Water soluble eosin, Xylidine ponceau, or Yellowish eosin.

In certain embodiments, the composition of the present disclosure includes any of the chromophores listed above, or a combination thereof, so as to provide a biophotonic impact at the treatment site. This is a distinct application of these agents and differs from the use of chromophores as simple stains or as a catalyst for photo-polymerization. In certain embodiments, the composition does not include compounds which can be polymerized or cross-linked through activation of the chromophore.

Without being bound to any particular theory, a synergistic effect of the chromophore combinations means that the biophotonic effect is greater than the sum of their individual effects. Advantageously, this may translate to increased reactivity of the biophotonic material, faster or improved treatment time. Also, the treatment conditions need not be altered to achieve the same or better treatment results, such as time of exposure to light, power of light source used, and wavelength of light used. In other words, use of synergistic combinations of chromophores may allow the same or better treatment without necessitating a longer time of exposure to a light source, a higher power light source or a light source with different wavelengths.

In some embodiments, the material includes Eosin Y as a first chromophore and any one or more of Rose Bengal, Fluorescein, Erythrosine, Phloxine B, chlorophyllin as a second chromophore. It is believed that these combinations have a synergistic effect as they can transfer energy to one another when activated due in part to overlaps or close proximity of their absorption and emission spectra. This transferred energy is then emitted as fluorescence or leads to production of reactive oxygen species. This absorbed and re-emitted light is thought to be transmitted throughout the composition, and also to be transmitted into the site of treatment.

In further embodiments, the material includes the following synergistic combinations: Eosin Y and Fluorescein; Fluorescein and Rose Bengal; Erythrosine in combination with Eosin Y, Rose Bengal or Fluorescein; Phloxine B in combination with one or more of Eosin Y, Rose Bengal, Fluorescein and Erythrosine. Other synergistic chromophore combinations are also possible.

By means of synergistic effects of the chromophore combinations in the material, chromophores which cannot normally be activated by an activating light (such as a blue light from an LED), can be activated through energy transfer from chromophores which are activated by the activating light. In this way, the different properties of photoactivated chromophores can be harnessed and tailored according to the cosmetic or the medical therapy required.

For example, Rose Bengal can generate a high yield of singlet oxygen when activated in the presence of molecular oxygen; however it has a low quantum yield in terms of emitted fluorescent light. Rose Bengal has a peak absorption around 540 nm and so can be activated by green light. Eosin Y has a high quantum yield and can be activated by blue light. By combining Rose Bengal with Eosin Y, one obtains a composition which can emit therapeutic fluorescent light and generate singlet oxygen when activated by blue light. In this case, the blue light photoactivates Eosin Y which transfers some of its energy to Rose Bengal as well as emitting some energy as fluorescence.

The present disclosure provides biophotonic compositions that comprise at least a first chromophore and a tissue filler medium. The tissue filler medium may be a dermal filler. In some embodiments, the tissue filler medium is characterized by its source. In some embodiments, the source can be natural, biologic or synthetic. Biologic tissue filler media can be those that are derived from a living organism. In some embodiments, the tissue filler medium can be characterized by the body's ability to clear a product without external intervention (e.g., biodegradable vs. non-biodegradable). The tissue filler media and/or the biophotonic composition is generally biocompatible. The tissue filler media and/or the biophotonic composition is generally non-toxic. The tissue filler medium may comprise a polymer. The polymer may be selected from the group of polymers consisting of proteins, peptides, polypeptides, polylysine, collagens, pro-collagens, elastins, and laminins. The polymer may be selected from the group of polymers consisting of synthetic polymers with hydroxyl, amine, and carboxyl functional groups: poly(vinyl alcohol), polyethylene glycol, polyvinlyl amine, polyallylamine, deacetylated polyacrylamide, polyacrylic acid, and polymethacrylic acid. The polymer may be selected from the group of polymers consisting of dendritic or branched polymers, including dendritic polyols and dendritic polyamines. The polymer may be selected from the group of polymers consisting of solid surface with hydroxyl, amine, and carboxyl functional groups. The polymer may be a polysaccharide, for example, selected from the group of polysaccharides including starch and its derivatives; dextran and its derivatives, cellulose and its derivatives; chitin and chitosan and alginate and its derivatives. In some embodiments, the tissue filler medium is a cross-linked biocompatible polysaccharide gel.

In some embodiments, the polymer is a glycosaminoglycan. The tissue filler medium can further comprise two or more different glycosaminoglycan polymers. As used herein, the term "glycosaminoglycan" is synonymous with "GAG" and "mucopolysaccharide" and refers to long unbranched polysaccharides consisting of a repeating disaccharide units. The repeating unit consists of a hexose (six-carbon sugar) or a hexuronic acid, linked to a hexosamine (six-carbon sugar containing nitrogen) and pharmaceutically acceptable salts thereof. Members of the GAG family vary in the type of hexosamine, hexose or hexuronic acid unit they contain, such as, e.g., glucuronic acid, iduronic acid, galactose, galactosamine, glucosamine) and may also vary in the geometry of the glycosidic linkage. Non-limiting examples of glycosaminoglycans include chondroitin sulfate, dermatan sulfate, keratan sulfate, and hyaluronan. Non-limiting examples of an acceptable salt of a glycosaminoglycans includes sodium salts, potassium salts, magnesium salts, calcium salts, and combinations thereof. Glycosaminoglycan and their resulting polymers useful in the compositions and methods disclosed herein are described in, e.g., Piron and Tholin, Polysaccharide Cross-linking, Hydrogel Preparation, Resulting Polysaccharides(s) and Hydrogel(s), uses Thereof, U.S. Patent Publication 2003/0148995; Lebreton, Cross-Linking of Low and High Molecular Weight Polysaccharides Preparation of Injectable Monophase Hydrogels; Lebreton, Viscoelastic Solutions Containing Sodium Hyaluronate and Hydroxypropyl Methyl Cellulose, Preparation and Uses, U.S. Patent Publication 2008/0089918; Lebreton, Hyaluronic Acid-Based Gels Including Lidocaine, U.S. Patent Publication 2010/0028438; and Polysaccharides and Hydrogels thus Obtained, U.S. Patent Publication 2006/0194758; and Di Napoli, Composition and Method for Intradermal Soft Tissue Augmentation, International Patent Publication WO 2004/073759, each of which is hereby incorporated by reference in its entirety. GAGs useful in the methods disclosed herein are commercially available, such as, e.g., hyaluronan-based dermal fillers JUVEDERM™, JUVEDERM™ 30, JUVEDERM™ Ultra, JUVEDERM™ Ultra Plus, JUVEDERM™ Ultra XC, JUVEDERM™ Ultra Plus XC, JUVEDERM VOLUMA™ XC, and JUVEDERM VOLUMA™ (Allergan Inc., Irvine, Calif.).

Examples of biologic, biodegradable tissue filler media are those that include materials derived from organism, human, and/or animal tissues and/or products. Examples of such media include the following: hyaluronic acid (HA), (such as the following: avian HA, bovine HA, and non-animal stabilized HA ("NASHA") (e.g., RESTYLANE®, Captique® and Juvederm® injectable dermal fillers)), collagen (such as collagen I, collagen II, collagen III, cross-linked and/or non-cross-linked, bovine, porcine, human, and autologous collagen). Additional examples of collagen based fillers include ZYPLAST® (collagen derived from bovine tissue), ZYDERM® I (collagen derived from bovine tissue), ZYDERM® II, (collagen derived from bovine tissue), EVOLENCE™ (porcine derived collagen), and FIBREL™ (porcine derived collagen). Collagen-based tissue fillers are generally animal derived and have been associated with a higher occurrence of allergic reactions than non-animal based fillers. NASHA tissue fillers, for example, are bacteria derived and have a lower incidence of allergic reaction than the collagen-based fillers. Many NASHA tissue fillers provide an immediate filling effect but can also induce minimal collagen formation due to local mechanical deformation of fibroblasts at the soft tissue site. As can be appreciated by one of skill in the art, in some embodiments, the filler media is self-replicating, and can include living cells (such as collagen-producing cells or fibroblasts). Thus, in some embodiments the composition comprises a tissue filler medium that is biologic and biodegradable.

Synthetic, biodegradable, tissue filler media include RADIANCE™ and RADIESSE™ (calcium and phosphate based microspheres), LARESSE® (carboxymethyl cellulose and polyethylene oxide), SCULPTRA® (microspheres of poly-L-lactic acid), other polyacids, polyethers and polymers. The calcium and phosphate based microspheres comprise calcium hydroxylapatite particles suspended in a water-based gel that acts as a scaffold for new collagen growth. The particles degrade over time into calcium and phosphate ions which can be removed by normal metabolic processes. Degradation typically takes up to 18 months or even longer. Fillers based on poly-L-lactic acid are considered as "stimulatory" as they are thought to stimulate collagen production over time. Therefore, an immediate filling effect is not seen. Also, they have been associated with granuloma and nodule formation.

Synthetic, non-biodegradable, tissue filler media include compounds that are not readily broken down in the body. Synthetic, non-biodegradable, tissue filler media can include a biologic component (and vice versa). In some embodiments, at least a portion of the product cannot be significantly broken down by various body processes. Examples of synthetic non-biodegradable filler media include the following: ARTEFIL™ and ARTECOL™ (polymethylmethacrylate (PMMA) microspheres suspended in bovine collagen carrier), SILSKIN® (liquid medical grade silicone), DERMALIVE™ and DERMADEEP™ (stabilized hyaluronic acid plus acrylic hydrogel hydroxyethylmethacrylate (HEMA) and ethylmethacrylate (EMA) co-polymer particles) and various other polymers, polyacids, and polyethers. In some embodiments, the carrier has rapid biodegradation. Some of these non-degradable fillers will stimulate a fibroblastic deposition of collagen around the non-degradable material as part of the body's immune response. In some cases, the newly formed collagen may not be closely matched in type, fibrillar alignment and/or mechanical properties to the body's native collagen matrix. Also, complications may arise due to the non-degradable nature of the material and may be longer lasting and more difficult to treat than with degradable fillers. Furthermore, permanent fillers have also been associated with severe fibrotic reactions leading in some cases to scarring.

As can be appreciated by one of skill in the art, in some embodiments, any one, or combination, of ingredients of the above fillers can be combined with the other fillers (or alternative fillers) in various embodiments and for particular results.

In some embodiments, the tissue filler media is selected from the following: collagen, fat, human or animal derived collagen, bovine collagen, type I collagen, type II collagen, type III collagen, 3.5% bovine dermal collagen cross-linked by glutaraldehyde to form a latticework, natural human collagen, autologous collagen, polymethylmethacrylate microspheres (optionally suspended in bovine collagen), suspension of collagen fibers prepared from the subject's tissue, human tissue collagen matrix derived from cadaveric dermis, polyacids and polyethers (e.g., carboxymethyl cellulose (CMC) and polyethylene oxide), acellular human cadaveric dermis that has been freeze-dried, micronized acellular human cadaveric dermis that has been freeze-dried, cultured autologous fibroblasts, hyaluronic acid, non-animal-stabilized hyaluronic acid derivative, microspheres of calcium hydroxyl apatite suspended in an aqueous gel carrier, dextran beads suspended in hylan gel of nonanimal origin (e.g., 40- to 60-μm in diameter), solubilized elastin peptides with bovine collagen, silicone, solubilized elastin peptides with bovine collagen, poly-L-lactic acid, polytetrafluoroethylene (PTFE), glycosylated collagen, PMMA, bone-forming calcium apatite, cultured human cells, expanded PTFE (e-PTFE), SOFTFORM® of ePTFE, and some combination thereof. Further examples of injectable filler media include the following: AQUAMID® (comprising water and cross-linked polymers), ARTEFIL® (PMMA microspheres suspended in bovine collagen), LARESSE® Dermal Filler (synthetic, biocompatible polymers, non-HA gel comprising absorbable medical polymers), ARTECOLL® (PMMA microspheres suspended in bovine collagen), BELOTERO®, BIO-ALCAMID™ (synthetic reticulate polymer (poly-alkyl-imide), CAPTIQUE™ (non-animal hyaluronic acid), COSMODERM™ (human collagen skin filler), COMOPLAST™, CYMETRA®, autologen, DERMALOGEN®, FASCIAN™ (fascia), fascia, fat, Hylaform™ (avian hyaluronic acid), JUVEDERM®, JUVEDERM VOLBELLA, JUVEDERM VOLUMA, JUVADERM ESTHELIS, JUVADERM FORTELIS, RESTYLANE®, PERLANE® (biosynthesized, non-animal hyaluronic acid), RADIESSE™ (microspheres based on calcium and phosphate), SCULPTRA® (poly-L-lactic acid (PLLA)), collagen, hyaluronic acid, ZYDERM®, ZYPLAST® (collagen derived from bovine tissue), DERMALIVE®, (hyaluronic acid and acrylic hydrogel particles), DERMADEEP® (hyaluronic acid and acrylic hydrogel particles), HYDRAFILL®, ISOLAGEN® (cultured autologous human fibroblasts), LARESSE® (carboxymethylcellulose (CMC) and polyethylene oxide (PEO) filler), PURAGEN™ (filler comprising double cross-linked hyaluron molecules), REVIDERM® INTRA (filler comprising flexible dextran micro-beads suspended in super-coiled, stabilized hyaluronic acid), SCULPTRA™ (Formerly NEW-FILL™, filler from poly-L-lactic acid), Teosyal, SURGIDERM® (hyaluronic acid filler involving 3D hyaluronic acid matrix technology), OUTLINED, ANIKA®, Cosmetic tissue augmentation (CTA, from Anika), and combinations thereof.

Other examples of tissue fillers include: Juvederm® VOLIFT® from Allergan, Emervel® from Galderm, Elevess® from Anika Therapeutics, Regenovue® from Neogenesis.

In some embodiments, additional agents may be combined with the tissue filler medium. The agent combined with the polymer may comprise an anaesthetizing agent or a painkilling agent (e.g. lidocaine), or a vitamin (e.g. vitamin C). The additional agent may comprise a biologically active component such as growth factors, peptides and cells.

In some embodiments, the tissue filler medium is substantially stable at room temperature for, e.g., about 3 months, about 6 months, about 9 months, about 12 months, about 15 months, about 18 months, about 21 months, about 24 months, about 27 months, about 30 months, about 33 months, or about 36 months. In other aspects of this embodiment, a dermal filler composition is substantially stable at room temperature for, e.g., at least 3 months, at least 6 months, at least 9 months, at least 12 months, at least 15 months, at least 18 months, at least 21 months, at least 24 months, at least 27 months, at least 30 months, at least 33 months, or at least 36 months. In other aspects of this embodiment, a tissue filler composition is substantially stable at room temperature for, e.g., about 3 months to about 12 months, about 3 months to about 18 months, about 3 months to about 24 months, about 3 months to about 30 months, about 3 months to about 36 months, about 6 months to about 12 months, about 6 months to about 18 months, about 6 months to about 24 months, about 6 months to about 30 months, about 6 months to about 36 months, about 9 months to about 12 months, about 9 months to about 18 months, about 9 months to about 24 months, about 9 months to about 30 months, about 9 months to about 36 months, about 12 months to about 18 months, about 12 months to about 24 months, about 12 months to about 30 months, about 12 months to about 36 months, about 18 months to about 24 months, about 18 months to about 30 months, or about 18 months to about 36 months.

In some embodiments, the tissue filler medium is degradable and degrades in vivo in about 1 month, 2 months, 3 months, about 3 months to about 12 months, about 3 months to about 18 months, about 3 months to about 24 months, about 6 months to about 12 months, about 6 months to about 18 months, about 9 months to about 12 months, about 9 months to about 18 months, about 12 months to about 18 months.

In certain embodiments, the tissue filler medium comprises cross-linked hyaluronic acid. The hyaluronic acid may be non-animal derived such as through a streptococcal fermentation process which is then stabilized by cross-linking. Such bacterially derived hyaluronic acids have a shorter chain length and molecular weight than animal based hyaluronic acid (about 1-3 megadaltons compared with 4-6 megadaltons).

Cross-linking of hyaluronic acid can be achieved using cross-linking agents such as 1, 4-butanediol diglycidyl ether (BDDE) (e.g. Restylane, Juvederm and Boletero dermal fillers), divinyl sulphone (DVS) (e.g. Hylaform, Captique and Prevelle dermal fillers), 2, 7, 8-diepoxyoctane (DEO), a polyethylene glycol based crosslinking agent as described in U.S. Patent Application Publication No: 2014/0039062, the contents of which are incorporated herein by reference, and biscarbodiimide in the presence of a pH buffer, as described in U.S. Pat. No. 8,124,120, the contents of which are incorporated herein by reference. Cross-linking renders the hyaluronic acid slower to degrade. The type and extent of cross-linking will determine the rate of degradation, viscoelastic properties as well as the stability of the tissue filler medium. However, a possible limitation on the extent of cross-linking may be a decrease in biocompatibility (e.g. increased inflammatory response and granuloma formation in vivo) and a high viscosity rendering the filler non-injectable.

The tissue filler medium may comprise a relatively insoluble cross-linked hyaluronic acid component within a soluble fluid component. The cross-linked hyaluronic acid component may comprise cohesive particles. The soluble fluid component may comprise free hyaluronic acid (non cross-linked) or any other fluid component which can facilitate the delivery of the tissue filler composition through fine bore needles. The concentration of hyaluronic acid (including both cross-linked and non cross-linked hyaluronic acid components) can vary from about 4.5 to about 40 mg/mL, about 4.5 to about 35 mg/mL, about 4.5 to about 30 mg/mL, about 4.5 to about 25 mg/mL, about 4.5 to about 20 mg/mL, about 4.5 to about 15 mg/mL, about 4.5 to about 10 mg/mL. The concentration of hyaluronic acid (including both cross-linked and non cross-linked hyaluronic acid components) can be about 10 mg/mL, about 12 mg/mL, about 14 mg/mL, about 16 mg/mL, about 18 mg/mL, about 20 mg/mL, about 22 mg/mL, or about 24 mg/mL. The non cross-linked hyaluronic acid component may comprise from about 30% to about 100% of the total hyaluronic acid, or about 40-100%, about 40-99%, about 40-98%, about 40-95%, about 40-90%, about 40-85%, about 40-80%, about 40-75%, about 40-70%, about 40-65%, about 40-60%, about 40-55%, about 40-50%, about 40-45%, about 50-100%, about 50-99%, about 50-98%, about 50-95%, about 50-90%, about 50-85%, about 50-80%, about 50-75%, about 50-70%, about 50-65%, about 50-60%, about 50-55%, about 60-100%, about 60-99%, about 60-98%, about 60-95%, about 60-90%, about 60-85%, about 60-80%, about 60-75%, about 60-70% of the total hyaluronic acid content in the composition. The cross-linked hyaluronic acid component may comprise from about 1% to about 20% of the total hyaluronic acid content in the composition. In certain embodiments, the cross-linked hyaluronic acid component comprises from about 1% to about 15%, about 1% to about 14%, about 1% to about 13%, about 1% to about 12%, about 1% to about 11%, about 1% to about 10%, about 1% to about 9%, about 1% to about 8%, about 1% to about 7%, about 1% to about 6%, about 1% to about 5%, about 1% to about 4%, about 1% to about 3%, about 1% to about 2%. In certain embodiments, the cross-linked hyaluronic acid component comprises from about 1% to about 12%, about 3% to about 10%, or about 4% to about 10%.

In certain embodiments, the tissue filler medium comprises cross-linked hyaluronic acid particles within a fluid component, the particles may be the same or different sizes. The particles may be sized to enable them to pass through a fine needle bore such as a 27-40 G needle. The particle sizes may range from 100-1000 microns, or about 200-1000 microns, about 250-1000 microns, about 300-1000 microns, about 350-1000 microns, about 400-1000 microns about 450-1000 microns, about 500-1000 microns, about 550-1000 microns, about 600-1000 microns, about 650-1000 microns, about 700-1000 microns, about 200-900 microns, about 250-900 microns, about 300-900 microns, about 350-900 microns, about 400-900 microns about 450-900 microns, about 500-900 microns, about 550-900 microns, about 600-900 microns, about 650-900 microns, about 700-900 microns, 200-800 microns, about 250-800 microns, about 300-800 microns, about 350-800 microns, about 400-800 microns about 450-800 microns, about 500-800 microns, about 550-800 microns, about 600-800 microns, about 650-800 microns, or about 700-800 microns.

Cohesiveness of the tissue filler composition may be a desired property in applications where it is desired to mechanically lift soft tissue around the implantation or injection site. The elastic modulus G' is often used to characterize the firmness of a gel, and represents the material's ability to resist deformation. In hyaluronic gels, the degree of cross-linking and hyaluronic acid concentration affects the modulus of the composition. Increasing hyaluronic acid concentration and cross-linking will increase the filler modulus. In certain embodiments, the elastic modulus, G', of the tissue filler media ranges from 100-800 Pa, about 100-700 Pa, about 100-600 Pa, about 100-500 Pa, about 200-600 Pa, or about 200-500 Pa.

In certain embodiments, the tissue filler medium is hydrated. The extent of hydration is a factor in determining how much the medium will swell once administered to soft tissue.

The biophotonic compositions of the present disclosure have numerous uses. Without being bound by theory, the biophotonic compositions of the present disclosure may be used for skin rejuvenation. The biophotonic compositions of the present disclosure may promote wound healing or tissue repair. The biophotonic compositions of the present disclosure may provide cosmetic enhancement of soft tissue. The biophotonic compositions of the present disclosure may inhibit or treat scarring. The biophotonic compositions of the present disclosure may stimulate collagen synthesis. This collagen synthesis may be useful for tissue repair, skin rejuvenation, or cosmetic enhancement of soft tissue. Therefore, it is an objective of the present disclosure to provide a method for providing biophotonic therapy to a wound, where the method promotes wound healing. It is an objective of the present disclosure to provide a method for providing biophotonic therapy to a wound, where the method promotes collagen synthesis. It is an objective of the present disclosure to provide a method for providing biophotonic therapy to a wound, where the method prevents scar formation. It is also an objective of the present disclosure to provide a method for providing biophotonic therapy to skin tissue, wherein the method is used for promoting skin rejuvenation. It is also an objective of the present disclosure to provide a method for providing biophotonic therapy to skin tissue, wherein the method is used for promoting collagen synthesis.

In certain embodiments, the present disclosure provides a method for providing a biophotonic therapy to a wound, the method comprising: administering a composition to an area to be treated within a wound, wherein the composition comprises a tissue filler medium and a fluorophore; illuminating the area with light having a wavelength which can be absorbed by the fluorophore; wherein the method stimulates wound healing in the area.

In yet another aspect, the present disclosure provides a method for promoting skin rejuvenation. In certain embodiments, the present disclosure provides a method for providing skin rejuvenation, the method comprising: administering a composition to an area to be treated within a soft tissue, wherein the composition comprises a tissue filler medium and a fluorophore; illuminating the area with light having a wavelength which can be absorbed by the fluorophore; wherein the method stimulates collagen synthesis in the area. The tissue filler medium may provide an immediate filling effect and the composition may induce collagen synthesis.

In yet another aspect, the present disclosure provides a method for cosmetic enhancement of soft tissue. In certain embodiments, the present disclosure provides a method for cosmetic enhancement of soft tissue comprising: intradermally or subdermally administering a composition to an area to be treated, wherein the composition comprises a tissue filler medium and a fluorophore; illuminating the area with light having a wavelength which can be absorbed by the fluorophore; wherein the method stimulates collagen synthesis in the area to cosmetically enhance the soft tissue.

In yet another aspect, the present disclosure provides a method for inhibiting or treating scarring. In certain embodiments, the present disclosure provides a method for inhibiting or treating scarring, the method comprising: administering a composition to an area to be treated within or around a scar or a wound, wherein the composition comprises a tissue filler medium and a fluorophore; illuminating the area with light having a wavelength which can be absorbed by the fluorophore; wherein the method stimulates collagen synthesis in the area to prevent or reduce scar formation.

In the methods disclosed herein, the biophotonic composition can be administered by injection or implantation (e.g., using a syringe and needle, etc.) into or underneath soft tissue at a treatment site (e.g., subcutaneous administration, intradermal administration, subdermal administration). A skilled person can select an appropriate needle bore size according to the soft tissue to be treated. In intradermal applications, needle gauges of 27 G to 40 G can be used, typically 30 or 32 G. The higher the gauge size, the finer the needle bore. The biophotonic compositions of the disclosure can also be injected or implanted superficially, such as, for example, within the papillary layer of the dermis, or can be injected or implanted within the reticular layer of the dermis.

The biophotonic composition can be administered intradermally or subdermally into the dermis in a continuous fashion (e.g. linear threading) or using pin pricks to form discrete pockets of the biophotonic composition intradermally or subdermally (e.g. serial puncture technique). The biophotonic composition can be illuminated at the same time as administering the composition to the soft tissue site, or after administration.

In certain embodiments, about 1 mL of the biophotonic composition is administered intradermally or subdermally. In certain embodiments, less than about 1 mL of the biophotonic composition is administered intradermally or subdermally. In certain embodiments, about 0.1-0.2, about 0.2-0.3, about 0.3-0.4, about 0.4-0.5, about 0.5-0.6, about 0.6-0.7, about 0.7-0.8, about 0.8-0.9, about 0.9-1.0 mL of the biophotonic composition is administered intradermally or subdermally.

The biophotonic compositions suitable for use in the methods of the present disclosure may be selected from any of the embodiments of the biophotonic compositions described above. For instance, the biophotonic compositions useful in the method of the present disclosure may comprise a first chromophore that undergoes at least partial photobleaching upon application of light. The first chromophore may absorb at a wavelength of about 200-800 nm, about 200-700 nm, about 200-600 nm or about 200-500 nm. In one embodiment, the first chromophore absorbs at a wavelength of about 200-600 nm. In some embodiments, the first chromophore absorbs light at a wavelength of about 200-300 nm, about 250-350 nm, about 300-400 nm, about 350-450 nm, about 400-500 nm, about 450-650 nm, about 600-700 nm, about 650-750 nm or about 700-800 nm. In other examples, suitable biophotonic compositions for the methods of the present disclosure may further comprise at least one additional chromophore (e.g., a second chromophore). The absorption spectrum of the second chromophore overlaps at least about 80%, at least about 50%, at least about 40%, at least about 30%, or at least about 20% with the emission spectrum of the first chromophore. In some embodiments, the first chromophore has an emission spectrum that overlaps at least about 1-10%, at least about 5-15%, at least about 10-20%, at least about 15-25%, at least about 20-30%, at least about 25-35%, at least about 30-40%, at least about 35-45%, at least about 50-60%, at least about 55-65% or at least about 60-70% with an absorption spectrum of the second chromophore.

Illumination of the biophotonic composition with light may cause a transfer of energy from the first chromophore to the second chromophore. Subsequently, the second chromophore may emit energy as fluorescence and/or generate reactive oxygen species. In certain embodiments of the methods of the present disclosure, energy transfer caused by the application of light is not accompanied by concomitant generation of heat, or does not result in tissue damage.

In the methods of the present disclosure, the biophotonic composition may be illuminated transdermally (from outside the body) or from within the soft tissue (e.g. using an optical fibre or a light duct). In certain embodiments, the biophotonic composition may itself form a light duct from the skin surface to the composition. To form such a light duct, a trail of the composition is formed from the skin puncture point to the composition within the soft tissue. In the methods of the present disclosure, the biophotonic composition may be illuminated at the same time as or immediately following administration of the composition to the intracorporeal area.

In the methods of the present disclosure, any source of actinic light can be used. Any type of halogen, LED or plasma arc lamp or laser may be suitable. The primary characteristic of suitable sources of actinic light will be that they emit light in a wavelength (or wavelengths) appropriate for activating the one or more photoactivators present in the composition. In one embodiment, an argon laser is used. In another embodiment, a potassium-titanyl phosphate (KTP) laser (e.g. a GreenLight™ laser) is used. In another embodiment, sunlight may be used. In yet another embodiment, a LED photocuring device is the source of the actinic light. In yet another embodiment, the source of the actinic light is a source of light having a wavelength between about 200 to 800 nm. In another embodiment, the source of the actinic light is a source of visible light having a wavelength between about 400 and 600 nm or about 400 to 700 nm. In yet another embodiment, the source of the actinic light is blue light. In yet another embodiment, the source of the actinic light is red light. In yet another embodiment, the source of the actinic light is green light. Furthermore, the source of actinic light should have a suitable power density. Suitable power density for non-collimated light sources (LED, halogen or plasma lamps) are in the range from about 1 $mW/cm^2$ to about 200 $mW/cm^2$.

Suitable power density for laser light sources are in the range from about 0.5 $mW/cm^2$ to about 0.8 $mW/cm^2$.

In some embodiments of the methods of the present disclosure, the light has an energy at the subject's skin, wound or mucosa surface of between about 1 $mW/cm^2$ and about 500 $mW/cm^2$, 1-300 $mW/cm^2$, or 1-200 $mW/cm^2$, wherein the energy applied depends at least on the condition being treated, the wavelength of the light, the distance of the subject's skin from the light source, and the thickness of the biophotonic composition. In certain embodiments, the light at the subject's skin is between about 1-40 $mW/cm^2$, or 20-60 $mW/cm^2$, or 40-80 $mW/cm^2$, or 60-100 $mW/cm^2$, or 80-120 $mW/cm^2$, or 100-140 $mW/cm^2$, or 120-160 $mW/cm^2$, or 140-180 $mW/cm^2$, or 160-200 $mW/cm^2$, or 110-240 $mW/cm^2$, or 110-150 $mW/cm^2$, or 190-240 $mW/cm^2$.

In some embodiments of the methods of the present disclosure, a biophotonic topical composition may be and additional source of illumination or the only source of illumination. In these embodiments, the biophotonic topical composition may comprise a fluorophore such that when illuminated with an activating light (e.g. from an LED or laser light source) it will emit light having a longer wavelength (Stoke's shift). The light from the activating light and/or the biophotonic topical composition may activate the fluorophore within the tissue filler composition. In this way, the tissues surrounding the tissue filler composition are illuminated with a broad bandwidth of light of different intensities. The topical biophotonic compositions may be as described in any one of WO 2010/051636, WO 2010/

051641 and WO 2013/155620, the contents of which are herein incorporated by reference.

In certain embodiments, the chromophore(s) in the composition can be photoexcited by ambient light including from the sun and overhead lighting. In certain embodiments, the chromophore(s) can be photoactivated by light in the visible range of the electromagnetic spectrum. The light can be emitted by any light source such as sunlight, light bulb, an LED device, electronic display screens such as on a television, computer, telephone, mobile device, flashlights on mobile devices. In the methods of the present disclosure, any source of light can be used. For example, a combination of ambient light and direct sunlight or direct artificial light may be used. Ambient light can include overhead lighting such as LED bulbs, fluorescent bulbs etc. and indirect sunlight.

The duration of the exposure to actinic light required will be dependent on depth beneath the skin surface of the biophotonic composition; the thickness, density and components of the intervening tissue; the type of intervening tissue, the concentration of chromophore within the tissue filler composition, the power density, wavelength and bandwidth of the light source, the thickness of the biophotonic composition, and the treatment distance from the light source. The illumination of the treated area by fluorescence may take place within seconds or even fragments of seconds, but a prolonged exposure period is beneficial to exploit the synergistic effects of the absorbed, reflected and reemitted light on the composition of the present disclosure and its interaction with the tissue being treated.

In one embodiment, the time of exposure to actinic light of the tissue in which the biophotonic composition has been administered is a period between 1 minute and 5 minutes. In another embodiment, the time of exposure to actinic light of the tissue in which the biophotonic composition has been administered is a period between 1 minute and 5 minutes. In some other embodiments, the biophotonic composition is illuminated for a period between 1 minute and 3 minutes. In certain embodiments, light is applied for a period of 1-30 seconds, 15-45 seconds, 30-60 seconds, 0.75-1.5 minutes, 1-2 minutes, 1.5-2.5 minutes, 2-3 minutes, 2.5-3.5 minutes, 3-4 minutes, 3.5-4.5 minutes, 4-5 minutes, 5-10 minutes, 10-15 minutes, 15-20 minutes, 20-25 minutes, or 20-30 minutes. The treatment time may range up to about 90 minutes, about 80 minutes, about 70 minutes, about 60 minutes, about 50 minutes, about 40 minutes or about 30 minutes. It will be appreciated that the treatment time can be adjusted in order to maintain a dosage by adjusting the rate of fluence delivered to a treatment area. For example, the delivered fluence may be about 4 to about 60 $J/cm^2$, about 10 to about 60 $J/cm^2$, about 10 to about 50 $J/cm^2$, about 10 to about 40 $J/cm^2$, about 10 to about 30 $J/cm^2$, about 20 to about 40 $J/cm^2$, about 15 $J/cm^2$ to 25 $J/cm^2$, or about 10 to about 20 $Ecm^2$.

In yet another embodiment, the source of actinic light is in continuous motion over the treated area for the appropriate time of exposure. In yet another embodiment, multiple applications of the biophotonic composition and actinic light are performed. In some embodiments, the biophotonic composition or the tissue is exposed to actinic light at least two, three, four, five or six times. In some embodiments, a fresh application of the topical biophotonic composition is applied before exposure to actinic light, or a fresh biophotonic composition administered to the soft tissues.

The method may be repeated as necessary. For example, in certain embodiments where the tissue filler medium is a biodegradable material, the method may be repeated close to or after full degradation of the tissue filler medium. The tissue filler medium degradation time depends on the type of filler medium and its inherent degradation properties such as viscosity, the quantity of filler in the soft tissues, its placement within the soft tissues, and the depth of the tissue. The period of repeating the method according to certain embodiments of the present disclosure can range from about 2 months up to about 24 months. In certain embodiments, the fluorophore is not degraded after illumination, in which case the composition can be re-illuminated until photobleaching.

The method may further comprise massaging the area once the composition has been administered.

The epidermis and the dermis are the first and second layers of skin, respectively. The dermis contains the structural elements of the skin, the connective tissue. There are various types of connective tissue with different functions. Elastin fibers give the skin its elasticity, and collagen gives the skin its strength.

The junction between the dermis and the epidermis is an important structure. The dermal-epidermal junction interlocks forming finger-like epidermal ridges. The cells of the epidermis receive their nutrients from the blood vessels in the dermis. The epidermal ridges increase the surface area of the epidermis that is exposed to these blood vessels and the needed nutrients.

Aging of skin comes with significant physiological changes to the skin. The generation of new skin cells slows down, and the epidermal ridges of the dermal-epidermal junction flatten out. While the number of elastin fibers increases, their structure and coherence decrease. Also the amount of collagen and the thickness of the dermis decrease with the ageing of the skin.

Collagen is a major component of the skin's extracellular matrix, providing a structural framework. During the aging process, the decrease of collagen synthesis and insolubilization of collagen fibers contribute to a thinning of the dermis and loss of the skin's biomechanical properties.

The physiological changes to the skin result in noticeable aging symptoms often referred to as chronological-, intrinsic- and photo-ageing. The skin becomes drier, roughness and scaling increase, the appearance becomes duller, and most obviously fine lines and wrinkles appear.

Other symptoms or signs of skin aging include, but are not limited to, thinning and transparent skin, loss of underlying fat (leading to hollowed cheeks and eye sockets as well as noticeable loss of firmness on the hands and neck), bone loss (such that bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, a blotchy complexion.

The dermal-epidermal junction is a basement membrane that separates the keratinocytes in the epidermis from the extracellular matrix, which lies below in the dermis. This membrane consists of two layers: the basal lamina in contact with the keratinocytes, and the underlying reticular lamina in contact with the extracellular matrix. The basal lamina is rich in collagen type IV and laminin, molecules that play a role in providing a structural network and bioadhesive properties for cell attachment.

Laminin is a glycoprotein that only exists in basement membranes. It is composed of three polypeptide chains (alpha, beta and gamma) arranged in the shape of an asymmetric cross and held together by disulfide bonds. The three chains exist as different subtypes which result in twelve different isoforms for laminin, including Laminin-1 and Laminin-5.

The dermis is anchored to hemidesmosomes, specific junction points located on the keratinocytes, which consist of a-integrins and other proteins, at the basal membrane keratinocytes by type VII collagen fibrils. Laminins, and particularly Laminin-5, constitute the real anchor point between hemidesmosomal transmembrane proteins in basal keratinocytes and type VII collagen.

Laminin-5 synthesis and type VII collagen expression have been proven to decrease in aged skin. This causes a loss of contact between dermis and epidermis, and results in the skin losing elasticity and becoming saggy.

Another type of wrinkles, generally referred to as expression wrinkles, require loss of resilience, particularly in the dermis, because of which the skin is no longer able to resume its original state when facial muscles which produce facial expressions exert stress on the skin, resulting in expression wrinkles.

The compositions and methods of the present disclosure promote skin rejuvenation. In certain embodiments, the compositions and methods of the present disclosure promote collagen synthesis. In certain other embodiments, the compositions and methods of the present disclosure may reduce, diminish, retard or even reverse one or more signs of skin aging including, but not limited to, appearance of fine lines or wrinkles, thin and transparent skin, loss of underlying fat (leading to hollowed cheeks and eye sockets as well as noticeable loss of firmness on the hands and neck), bone loss (such that bones shrink away from the skin due to bone loss, which causes sagging skin), dry skin (which might itch), inability to sweat sufficiently to cool the skin, unwanted facial hair, freckles, age spots, spider veins, rough and leathery skin, fine wrinkles that disappear when stretched, loose skin, or a blotchy complexion. In certain embodiments, the compositions and methods of the present disclosure may induce a reduction in pore size, enhance sculpturing of skin subsections, and/or enhance skin translucence. Furthermore, the compositions and methods of the present disclosure may enhance the cosmetic appearance of skin such as by improving luminosity and texture, reducing pore size, and tightening the skin.

The biophotonic materials and methods of the present disclosure may be used to treat wounds, promote wound healing, promote tissue repair and/or prevent or reduce cosmesis including improvement of motor function (e.g. movement of joints). Wounds that may be treated by the biophotonic materials and methods of the present disclosure include, for example, injuries to the skin and subcutaneous tissue initiated in different ways (e.g., pressure ulcers from extended bed rest, wounds induced by trauma or surgery, burns, ulcers linked to diabetes or venous insufficiency, wounds induced by conditions such as periodontitis) and with varying characteristics. In certain embodiments, the present disclosure provides biophotonic materials and methods for treating and/or promoting the healing of, for example, burns, incisions, excisions, lesions, lacerations, abrasions, puncture or penetrating wounds, surgical wounds, contusions, hematomas, crushing injuries, amputations, sores and ulcers.

Biophotonic compositions and methods of the present disclosure may be used to treat and/or promote the healing of chronic cutaneous ulcers or wounds, which are wounds that have failed to proceed through an orderly and timely series of events to produce a durable structural, functional, and cosmetic closure. The vast majority of chronic wounds can be classified into three categories based on their etiology: pressure ulcers, neuropathic (diabetic foot) ulcers and vascular (venous or arterial) ulcers.

For example, the present disclosure provides biophotonic compositions and methods for treating and/or promoting healing of a diabetic ulcer. Diabetic patients are prone to foot and other ulcerations due to both neurologic and vascular complications. Peripheral neuropathy can cause altered or complete loss of sensation in the foot and/or leg. Diabetic patients with advanced neuropathy lose all ability for sharp-dull discrimination. Any cuts or trauma to the foot may go completely unnoticed for days or weeks in a patient with neuropathy. A patient with advanced neuropathy loses the ability to sense a sustained pressure insult, as a result, tissue ischemia and necrosis may occur leading to for example, plantar ulcerations. Microvascular disease is one of the significant complications for diabetics which may also lead to ulcerations. In certain embodiments, biophotonic materials and methods of treating a chronic wound are provided here in, where the chronic wound is characterized by diabetic foot ulcers and/or ulcerations due to neurologic and/or vascular complications of diabetes.

In other examples, the present disclosure provides biophotonic compositions and methods for treating and/or promoting healing of a pressure ulcer. Pressure ulcers include bed sores, decubitus ulcers and ischial tuberosity ulcers and can cause considerable pain and discomfort to a patient. A pressure ulcer can occur as a result of a prolonged pressure applied to the skin. Thus, pressure can be exerted on the skin of a patient due to the weight or mass of an individual. A pressure ulcer can develop when blood supply to an area of the skin is obstructed or cut off for more than two or three hours. The affected skin area can turn red, become painful and necrotic. If untreated, the skin can break open and become infected. A pressure ulcer is therefore a skin ulcer that occurs in an area of the skin that is under pressure from e.g. lying in bed, sitting in a wheelchair, and/or wearing a cast for a prolonged period of time. Pressure ulcers can occur when a person is bedridden, unconscious, unable to sense pain, or immobile. Pressure ulcers often occur in boney prominences of the body such as the buttocks area (on the sacrum or iliac crest), or on the heels of foot.

Additional types of wounds that can be treated by the biophotonic materials and methods of the present disclosure include those disclosed by US Patent Application Publication No. 20090220450, which is incorporated herein by reference.

There are three distinct phases in the wound healing process. First, in the inflammatory phase, which typically occurs from the moment a wound occurs until the first two to five days, platelets aggregate to deposit granules, promoting the deposit of fibrin and stimulating the release of growth factors. Leukocytes migrate to the wound site and begin to digest and transport debris away from the wound. During this inflammatory phase, monocytes are also converted to macrophages, which release growth factors for stimulating angiogenesis and the production of fibroblasts.

Second, in the proliferative phase, which typically occurs from two days to three weeks, granulation tissue forms, and epithelialization and contraction begin. Fibroblasts, which are key cell types in this phase, proliferate and synthesize collagen to fill the wound and provide a strong matrix on which epithelial cells grow. As fibroblasts produce collagen, vascularization extends from nearby vessels, resulting in granulation tissue. Granulation tissue typically grows from the base of the wound. Epithelialization involves the migration of epithelial cells from the wound surfaces to seal the wound. Epithelial cells are driven by the need to contact cells of like type and are guided by a network of fibrin strands that function as a grid over which these cells migrate. Contractile cells called myofibroblasts appear in wounds, and aid in wound closure. These cells exhibit collagen synthesis and contractility, and are common in granulating wounds.

Third, in the remodeling phase, the final phase of wound healing which can take place from three weeks up to several years, collagen in the scar undergoes repeated degradation and re-synthesis. During this phase, the tensile strength of the newly formed skin increases.

However, as the rate of wound healing increases, there is often an associated increase in scar formation. Scarring is a consequence of the healing process in most adult animal and human tissues. Scar tissue is not identical to the tissue which it replaces, as it is usually of inferior functional quality. The types of scars include, but are not limited to, atrophic, hypertrophic and keloidal scars, as well as scar contractures. Atrophic scars are flat and depressed below the surrounding skin as a valley or hole. Hypertrophic scars are elevated scars that remain within the boundaries of the original lesion, and often contain excessive collagen arranged in an abnormal pattern. Keloidal scars are elevated scars that spread beyond the margins of the original wound and invade the surrounding normal skin in a way that is site specific, and often contain whorls of collagen arranged in an abnormal fashion.

In contrast, normal skin consists of collagen fibers arranged in a basket-weave pattern, which contributes to both the strength and elasticity of the dermis. Thus, to achieve a smoother wound healing process, an approach is needed that not only stimulates collagen production, but also does so in a way that reduces scar formation.

The biophotonic compositions and methods of the present disclosure promote wound healing by promoting the formation of substantially uniform epithelialization; promoting collagen synthesis; promoting controlled contraction; and/or by reducing the formation of scar tissue. In certain embodiments, the biophotonic compositions and methods of the present disclosure may promote wound healing by promoting the formation of substantially uniform epithelialization. In some embodiments, the biophotonic compositions and methods of the present disclosure promote collagen synthesis. In some other embodiments, the biophotonic compositions and methods of the present disclosure promote controlled contraction. In certain embodiments, the biophotonic compositions and methods of the present disclosure promote wound healing, for example, by reducing the formation of scar tissue. In certain embodiments, the biophotonic composition can be used during or following wound closure to optimize scar revision.

The biophotonic composition may be administered at regular intervals such as once a week, or at an interval deemed appropriate by the physician. Alternatively, once administered, the biophotonic composition may be light activated at regular intervals until exhaustion of the chromophore.

Adjunct therapies which may be topical or systemic such as antibiotic treatment may also be used. Negative pressure assisted wound closure can also be used to assist wound closure and/or to remove the composition.

In some instances, the frequency of administration of the biophotonic compositions as defined herein may depend on the type and/or the quantity of the filler that is initially administered. Fillers can be re-administered as early as a few months and as late as 2 years depending on their thickness, viscosity and elasticity. As such, the question of administrations per unit time may depend on the type of filler, the placement, the depth of tissue-site, and the quantity administered.

The present disclosure also provides kits for preparing and/or administering any of the compositions of the present disclosure. The kit may include a container comprising the biophotonic composition of the present disclosure. The container may be light impermeable, air-tight and/or leak resistant. Exemplary containers include, but are not limited to, syringes, vials, or pouches. In some embodiments, the tissue filler medium and the chromophore compositions are provided in separate containers, to be mixed by the user prior to administration. In some embodiments, the tissue filler medium and the chromophore compositions are provided in a single pre-mixed composition. In some embodiments, the kit comprises a handheld injection device.

In other embodiments, the kit comprises a systemic or topical drug for augmenting the treatment of the composition. For example, the kit may include a systemic or topical antibiotic or hormone treatment for acne treatment or wound healing.

Written instructions on how to use the biophotonic composition in accordance with the present disclosure may be included in the kit, or may be included on or associated with the containers comprising the compositions of the present disclosure.

In certain embodiments of the kit, the kit may further comprise a light source such as a portable light with a wavelength appropriate to activate the chromophore in the biophotonic composition. The portable light may be battery operated or re-chargeable.

In certain embodiments, the kit may further comprise one or more waveguides.

In certain embodiments, the kit may further comprise topical biophotonic compositions as described in any one of WO 2010/051636, WO 2010/051641 and WO 2013/155620, the contents of which are herein incorporated by reference.

Identification of equivalent compositions, methods and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

EXAMPLES

The examples below are given so as to illustrate the practice of this invention. They are not intended to limit or define the entire scope of this invention.

Example 1

Compositions according to the present disclosure comprising a fluorophore and dermal filler were prepared. The following combinations of dermal filler and fluorophore were used:
1) JUVEDERM VOLBELLA+Fluorescein+Eosin Y;
2) JUVEDERM VOLBELLA+Eosin Y+Eosin B;
3) JUVEDERM VOLBELLA+Eosin Y;
4) JUVEDERM VOLUMA+Fluorescein+Eosin Y;
5) JUVEDERM VOLUMA+Eosin Y;
6) JUVEDERM VOLUMA+Eosin Y+Eosin B;
7) ESTHELIS+Eosin Y+Fluorescein;

8) FORTELIS+Eosin Y+Fluorescein;
9) PERLANE®+Fluorescein+Eosin Y;
10) PERLANE®+Eosin Y+Eosin B;
11) PERLANE®+Eosin Y;
12) RESTYLANE®+Fluorescein+Eosin Y;
13) RESTYLANE®+Eosin Y+Eosin B; and
14) RESTYLANE®+Eosin Y.

For example, compositions 7) and 8) were prepared as follows:

7) 0.75 g FORTELIS as mixed with 9.38 μl Eosin Y (9.6 mg/ml) and 9.38 μl Fluorescein (9.6 mg/ml) so that the final concentration of Eosin Y is 0.012% and the final concentration of fluorescein is 0.012%.

8) 0.75 g ESTHELIS was mixed with 9.38 μl Eosin Y (9.6 mg/ml) and 9.38 μl Fluorescein (9.6 mg/ml) so that the final concentration of Eosin Y is 0.012% and the final concentration of fluorescein is 0.012%.

Example 2

Dermal filler-mediated effect on collagen type I and III gene expression level was assessed in Dermal Human Fibroblasts (DHF). Dermal filler gels were evaluated in vitro to assess their potential effect on collagen synthesis. Collagen is an essential component of the skin extracellular matrix (ECM) and an increase of collagen synthesis is favorable in skin rejuvenation.

JUVEDERM VOLUMA (VB), JUVADERM VOLBELLA (V15), RESTYLANE® (RL), ESTHELIS (EB) and a mixture of JUVADERM VOLBELLA (V15), RESTYLANE® (RL) and ESTHELIS (EB) (Gel A) were used as dermal filler gels in the study. The effect of dermal fillers on collagen synthesis was tested in dermal human fibroblasts (DHF). Collagen type I and type III mRNA were quantified by qRT-PCR. DHF were cultured on glass bottom dish. The dermal filler gels were applied on the other side of the glass dish (2 mm thick) and were illuminated for 5 min (300 sec) at 5 cm distance using blue visible light (KLOX THERA™ lamp). The tested dermal filler gels contained Eosin Y only or the combination of both, Eosin Y and Fluorescein (0.011% of each). Dermal filler gels without chromophore were used as controls.

DHF cells were also treated with light alone without the gel to assess the effect of the blue light illumination on collagen expression pattern. Sixteen hours post-illumination, cells were collected for RNA extraction and cDNA synthesis was performed. Collagen mRNA level under different conditions was assessed by qRT-PCR. TGF β1 (5 ng/ml) was used to trigger collagen genes expression and served as a positive control in all experiments. Results are presented as fold mRNA expression level compared to untreated control.

The data is summarized in the Table 1.

TABLE 1

Collagen type I and III mRNA expression in DHF 16 hours post-treatment compared to untreated control.

| Dermal filler gels | Type I collagen mRNA | Type III collagen mRNA |
| --- | --- | --- |
| Light (KLOX Thera ™ lamp) | 1.62 | 1.55 |
| VB + no chromophore | 0.46 | 1.1 |
| VB + Eosin Y | 2.48 | 1.16 |
| V15 + no chromophore | 0.47 | 1.58 |
| V15 + Eosin Y | 1.7 | 1.2 |
| V15 + Eosin Y + Fluorescein | 0.74 | 1.7 |
| RL + no chromophore | 1.17 | 0.75 |
| RL + Eosin Y | 1 | 0.8 |
| RL + Eosin Y + Fluorescein | 1.6 | 0.98 |
| EB + no chromophore | 1.29 | 1,46 |
| EB + Eosin Y + Fluorescein | 1.13 | 1.64 |
| Gel A + no chromophore | 2.3 | 1.57 |
| Gel A + Eosin Y + Fluorescein | 2.9 | 2.33 |

Gel A+Eosin Y+Fluorescein showed a positive effect on collagen type I and type III gene expression (up to 2.9 and 2.33 fold increase, respectively) as compared to untreated control. Interestingly, slight induction of the collagen type I and type III genes expression was also observed for Gel A no chromophore tested sample (2.3 and 1.57 respectively), which could be attributed to the higher ability of Gel A to transmit blue light which exerts its effect on DHF cells leading to collagen mRNA expression.

A mixture of tissue filler medium comprising EB, RL and V15 (Gel A) stimulated collagen type I mRNA expression in DHF cells to a higher level than the tissue filler medium applied individually as well as in comparison to light alone. Stimulation of collagen type I and collagen type III mRNA expression in DHF cells was increased when chromophores were added to Gel A, when compared to Gel A in absence of chromophores.

Example 3

The technique is performed under sterile conditions. The skin in the upper lip area is cleansed with chlorhexidine 0.5% (or similar antiseptic). At that time, a slow dermal or subdermal injection with the HA filler is undertaken. Care is taken not to overfill each area. Following completion of the injection, the area is gently massaged to achieve the desired result. The chromophore gel is applied and the area is illuminated using a LED light for a period of 5 minutes per region of the upper lip. Following the treatment with the light, the gel is removed with a saline wipe.

Example 4

A composition according to the present disclosure comprising a fluorophore and a dermal filler comprising hyaluronic acid may be injected intradermally under a fold on a patient's face. The composition may be illuminated with light overlapping the absorption spectra of the fluorophore to photoactivate the fluorophore in situ. The fluorophore may emit fluorescent light to the surrounding soft tissues.

Example 5

A composition according to the present disclosure comprising a fluorophore and a dermal filler comprising hyaluronic acid may be injected intradermally under a fold on a patient's face. A thin layer of a topical biophotonic composition may be placed over the fold, immediately above the injected composition. The topical composition may be illuminated with light overlapping the absorption spectra of a fluorophore in the topical composition to photoactivate the fluorophore and may cause it to emit light having emission spectra which may overlap the absorption spectra of the fluorophore within the injected composition of the present disclosure. The fluorophore may emit fluorescent light to the surrounding soft tissues.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

All documents mentioned in the specification are herein incorporated by reference.

The invention claimed is:

1. A method for stimulating collagen synthesis comprising:
   administering a composition to an area to be treated within a soft tissue, wherein the composition comprises a tissue filler medium, Eosin Y, and Fluorescein; and
   illuminating the area to be treated with light having a wavelength which can be absorbed by Eosin Y and Fluorescein;
   wherein the method stimulates collagen synthesis in the area to be treated.

2. A method for cosmetic enhancement of soft tissue comprising:
   intradermally or subdermally administering a composition to an area to be treated, wherein the composition comprises a tissue filler medium, Eosin Y, and Fluorescein; and
   illuminating the area to be treated with light having a wavelength which can be absorbed by Eosin Y and Fluorescein;
   wherein the method stimulates collagen synthesis in the area to be treated to cosmetically enhance the soft tissue.

3. The method of claim 1, wherein the area to be treated is soft tissue.

4. The method of claim 1, wherein the administering of the composition is by injection.

5. The method of claim 1, wherein the administering of the composition is by implantation.

6. The method of claim 1 or 2, wherein the composition is selected from a cohesive gel and a hydrated gel.

7. The method of claim 1 or 2, wherein the tissue filler is a dermal filler.

8. The method of claim 1 or 2, wherein the tissue filler medium comprises a polymer.

9. The method of claim 8, wherein the polymer is selected from proteins, peptides, polypeptides, polylysine, collagens, pro-collagens, elastins, and laminins.

10. The method of claim 8, wherein the polymer is selected from poly(vinyl alcohol), polyethylene glycol, polyvinlyl amine, polyallylamine, deacetylated polyacrylamide, polyacrylic acid, and polymethacrylic acid.

11. The method of claim 1 or 2, wherein the tissue filler medium comprises cross-linked hyaluronic acid.

12. The method of claim 1 or 2, wherein the composition further comprises light reflecting particles.

13. The method of claim 2, wherein intradermally or subdermally administering comprises providing a track of composition from external to the dermis to the composition.

14. A tissue filler composition comprising:
    a tissue filler medium; and
    at least Eosin Y and Fluorescein;
    wherein the composition is suitable for injection or implantation into a human.

15. The composition of claim 14, wherein the composition is a cohesive gel.

16. The composition of claim 14, wherein the composition is a hydrated gel.

17. The composition of claim 14, wherein the composition is transparent or translucent.

18. The composition of claim 14, wherein the tissue filler medium retains Eosin Y and Fluorescein within the composition during administering of the composition, and at least during a portion of the illumination.

19. The composition of claim 14, wherein the tissue filler medium is biodegradable.

20. The composition of claim 14, wherein the tissue filler medium comprises cross-linked hyaluronic acid.

21. The composition of claim 20, wherein the cross-linked hyaluronic acid is in particulate form.

22. The composition of claim 14, wherein the composition further comprises an injectable medium supporting the particles.

23. The composition of claim 14, wherein the injectable medium comprises hyaluronic acid which is relatively less cross-linked than the hyaluronic acid in particulate form.

24. The composition of claim 14, wherein the composition further comprises light reflecting particles.

25. The composition of claim 14, wherein Eosin Y and Fluorescein can be activated by light having a wavelength in the visible range.

26. The composition of claim 14, wherein Eosin Y and Fluorescein are not in a liposomal form in the composition.

* * * * *